US 008814869B2

(12) United States Patent
Freid et al.

(10) Patent No.: US 8,814,869 B2
(45) Date of Patent: Aug. 26, 2014

(54) SPINAL PLATE SYSTEM FOR STABILIZING A PORTION OF A SPINE

(75) Inventors: James M. Freid, Higley, AZ (US); Erik Wagner, Austin, TX (US); Jon P. Agricola, Skaneateles, NY (US); Alexander Vaccaro, Philadelphia, PA (US)

(73) Assignee: Zimmer Spine, Inc., Minneapolis, MN (US)

( * ) Notice: Subject to any disclaimer, the term of this patent is extended or adjusted under 35 U.S.C. 154(b) by 81 days.

(21) Appl. No.: 13/406,881

(22) Filed: Feb. 28, 2012

(65) Prior Publication Data
US 2012/0158059 A1 Jun. 21, 2012

Related U.S. Application Data

(63) Continuation of application No. 11/738,319, filed on Apr. 20, 2007, now Pat. No. 8,128,628, which is a continuation of application No. 10/351,288, filed on Jan. 24, 2003, now abandoned.

(60) Provisional application No. 60/353,272, filed on Feb. 1, 2002.

(51) Int. Cl.
*A61B 17/58* (2006.01)

(52) U.S. Cl.
USPC .................. 606/71; 606/280; 606/282

(58) Field of Classification Search
USPC ............................. 606/71, 280, 282
See application file for complete search history.

(56) References Cited

U.S. PATENT DOCUMENTS

| 1,073,714 | A | 9/1913 | Shorten |
| 2,507,681 | A | 5/1950 | Sage |
| 3,385,299 | A | 5/1968 | Le Roy |
| 3,604,414 | A | 9/1971 | Borges |
| 3,659,595 | A | 5/1972 | Haboush |
| 4,175,880 | A | 11/1979 | Muller |
| 5,129,903 | A | 7/1992 | Luhr |
| 5,364,396 | A | 11/1994 | Robinson et al. |
| 5,470,333 | A | 11/1995 | Ray et al. |
| 5,484,439 | A | 1/1996 | Olson et al. |
| 5,601,553 | A | 2/1997 | Trebing et al. |

(Continued)

FOREIGN PATENT DOCUMENTS

| DE | 4007306 C1 | 5/1991 |
| EP | 1478287 A4 | 8/2009 |

(Continued)

OTHER PUBLICATIONS

Atlantis Anterior Cervical Plate Ssystem brochure, Medtronic Sofamar Danek, Memphis, TN, 2000, 38 pages.

*Primary Examiner* — Nicholas Woodall
(74) *Attorney, Agent, or Firm* — Seager, Tufte & Wickhem, LLC

(57) ABSTRACT

A spinal plate system that maintains intervertebral spacing and spinal stability is provided. In an embodiment, a spinal compression plate may include two or more plates coupled together form an adjustable-length plate. Compression of a spinal compression plate movement may mimic natural settling of bones in a spine and/or distribute at least a portion of a vertebral load to an implant positioned between two vertebrae. Maintaining at least a portion of the vertebral load on an insert may increase bone growth and increase fusion between an implant and surrounding vertebrae.

13 Claims, 23 Drawing Sheets

(56) References Cited

U.S. PATENT DOCUMENTS

| | | | |
|---|---|---|---|
| 5,616,142 A | 4/1997 | Yuan et al. | |
| 5,622,177 A | 4/1997 | Breimesser et al. | |
| 5,672,177 A | 9/1997 | Seldin | |
| 5,735,853 A | 4/1998 | Olerud | |
| 5,827,286 A | 10/1998 | Incavo et al. | |
| 5,842,822 A | 12/1998 | Everett et al. | |
| 5,876,402 A | 3/1999 | Errico et al. | |
| 5,963,762 A | 10/1999 | Furuya et al. | |
| 6,051,007 A | 4/2000 | Hogendijk et al. | |
| 6,176,881 B1 | 1/2001 | Schär et al. | |
| 6,235,033 B1 | 5/2001 | Brace et al. | |
| 6,238,396 B1 | 5/2001 | Lombardo | |
| 6,306,136 B1 | 10/2001 | Baccelli | |
| 6,328,738 B1 | 12/2001 | Suddaby | |
| 6,331,179 B1 | 12/2001 | Freid et al. | |
| 6,402,756 B1 | 6/2002 | Ralph et al. | |
| 6,454,679 B1 | 9/2002 | Radow | |
| 6,454,769 B2 | 9/2002 | Wagner et al. | |
| 6,645,208 B2 | 11/2003 | Apfelbaum et al. | |
| 6,689,134 B2 | 2/2004 | Ralph et al. | |
| 6,852,113 B2 | 2/2005 | Nathanson et al. | |
| 6,932,820 B2 | 8/2005 | Osman | |
| 7,008,427 B2 | 3/2006 | Sevrain | |
| 7,044,952 B2 | 5/2006 | Michelson | |
| 7,097,645 B2 | 8/2006 | Michelson | |
| 7,118,573 B2 | 10/2006 | Michelson | |
| 7,591,840 B2 * | 9/2009 | Suddaby | 606/282 |
| 7,645,295 B2 | 1/2010 | Osman | |
| 7,695,473 B2 * | 4/2010 | Ralph et al. | 606/71 |
| 7,998,179 B2 * | 8/2011 | Lindemann et al. | 606/282 |
| 8,002,810 B2 | 8/2011 | Osman | |
| 8,348,949 B2 * | 1/2013 | Butler et al. | 606/71 |
| 2002/0055741 A1 | 5/2002 | Schlapfer | |
| 2002/0183755 A1 | 12/2002 | Michelson | |
| 2002/0183756 A1 | 12/2002 | Michelson | |
| 2002/0183757 A1 | 12/2002 | Michelson | |
| 2002/0188296 A1 | 12/2002 | Michelson | |
| 2003/0114856 A1 | 6/2003 | Nathanson et al. | |
| 2003/0130661 A1 | 7/2003 | Osman | |
| 2003/0199876 A1 | 10/2003 | Brace et al. | |
| 2003/0212399 A1 | 11/2003 | Dinh et al. | |
| 2004/0019353 A1 | 1/2004 | Freid et al. | |
| 2004/0092939 A1 | 5/2004 | Freid et al. | |
| 2005/0240184 A1 | 10/2005 | Osman | |
| 2006/0200134 A1 | 9/2006 | Freid et al. | |
| 2006/0235398 A1 * | 10/2006 | Farris et al. | 606/69 |
| 2008/0147125 A1 * | 6/2008 | Colleran et al. | 606/280 |
| 2009/0275988 A1 * | 11/2009 | Baynham | 606/282 |
| 2010/0137909 A1 | 6/2010 | Osman | |

FOREIGN PATENT DOCUMENTS

| | | |
|---|---|---|
| FR | 2751203 B1 | 12/1998 |
| WO | WO 9904718 A1 * | 2/1999 |
| WO | 0126566 A1 | 4/2001 |
| WO | 01089428 A3 | 8/2002 |
| WO | 03063714 A3 | 9/2003 |
| WO | 03071966 B1 | 12/2004 |
| WO | 2007035441 A1 | 3/2007 |

* cited by examiner

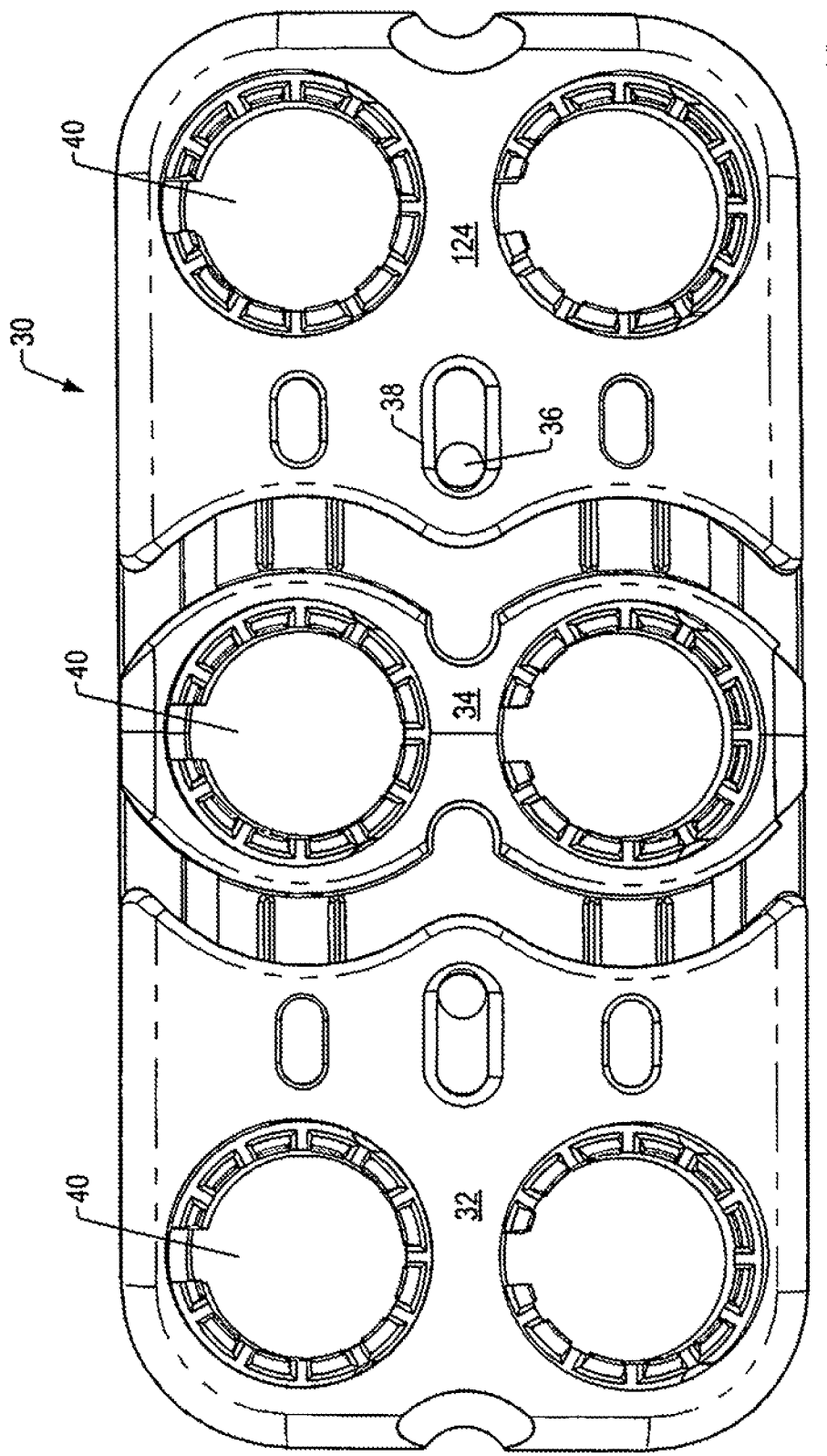

SPINAL PLATE SYSTEM FOR STABILIZING A PORTION OF A SPINE

CROSS-REFERENCE TO RELATED APPLICATIONS

This application is a continuation of U.S. patent application Ser. No. 11/738,319, filed on Apr. 20, 2007; which is a continuation of U.S. patent application Ser. No. 10/351,288, filed on Jan. 24, 2003; which claims priority to Provisional Patent Application No. 60/353,272, filed on Feb. 1, 2002; the entire disclosures of which are incorporated herein by reference.

BACKGROUND

1. Field of the Invention

The present invention generally relates to bone fixation systems. An embodiment of the invention relates to a compression plate for a spinal fixation system. The compression plate may be installed using an anterior procedure. The compression plate may be used in conjunction with one or more spinal implants that fuse vertebrae together.

2. Description of Related Art

An intervertebral disc may be subject to degeneration caused by trauma, disease, and/or aging. A degenerated intervertebral disc may have to be partially or fully removed from a spinal column. Partial or full removal of an intervertebral disc may destabilize a spinal column. Destabilization of a spinal column may alter a natural separation distance between adjacent vertebrae. Maintaining a natural separation distance between vertebrae may help prevent pressure from being applied to nerves that pass between vertebral bodies. Excessive pressure applied to the nerves may cause pain and/or nerve damage. During a spinal fixation procedure, a spinal implant may be inserted in a space created by removal or partial removal of an intervertebral disc between adjacent vertebrae. A spinal implant may maintain the height of the spine and restore stability to the spine. Intervertebral bone growth may fuse the implant to adjacent vertebrae.

A spinal implant may be inserted during a spinal fixation procedure using an anterior, lateral, or posterior spinal approach. In some situations, an anterior approach may result in an easier approach, less muscle damage, less tissue damage, and/or less bone removal than other approaches.

A discectomy may be performed to remove or partially remove a defective and/or damaged intervertebral disc. A discectomy creates a disc space for a spinal implant. After a discectomy, a spinal implant may be inserted into the disc space. One or, more spinal implants may be inserted between a pair of vertebrae. Spinal implants may be inserted into disc spaces prepared between more than one pair of vertebrae during a spinal fusion procedure.

A spinal plate may be coupled to vertebrae after insertion of one or more spinal implants. A spinal plate may stabilize the vertebrae and inhibit backout of the spinal implant from between vertebrae. A spinal plate may share a compressive load applied to one or, more spinal implants inserted between vertebrae. Fasteners (e.g., bone screws) may couple the spinal plate to vertebrae. Spinal plates may stabilize sections of cervical spine and/or sections of lumbar, spine.

Fastening systems may attach a spinal plate to vertebrae without allowing fasteners of the fastening systems to back out from the vertebrae. A fastening system may include a fastener and a retainer. The retainer may be positioned in an opening of the spinal plate. Backout of fasteners from the spinal plate may be inhibited without immovably fixing the fasteners or the retainers to the spinal plate. U.S. Pat. No. 6,331,179 to Freid et al. and U.S. Pat. No. 6,454,679 to Wagner et al., both of which are incorporated by reference as if fully set forth herein, describe bone plate systems including fasteners and retainers.

U.S. Pat. No. 6,328,738 to Suddaby, which is incorporated by reference as if fully set forth herein, describes an anterior cervical fusion compression plate and screw guide. The anterior cervical fusion compression plate has a pair of slideable inserts. Each insert is situated in a recess at an end of the plate to allow vertebral compression. During an insertion procedure, a pliers-like tool is used to move the inserts toward the center of the plate. After a desired compression is achieved, central screws are tightened to fix the position of the inserts. Lateral screws may be driven into the inserts to anchor the vertebrae to the plate.

SUMMARY

An adjustable-length spinal compression plate may be used to stabilize vertebrae and/or apply a compressive load to a spinal implant positioned in a disc space between a pair of vertebrae. One or more fasteners may couple a first plate to a vertebra above a spinal implant. One or more fasteners may couple a second plate to a vertebra below a spinal implant. The first plate may be coupled to the second plate so that the first plate is able to move toward and/or away from the second plate. In some embodiments, motion of the first plate relative to the second plate may be restricted to allow only unidirectional motion (i.e., only compression of the spinal compression plate) during use. Movement of the first plate toward the second plate may allow the spinal plate system to accommodate settling and/or subsidence of the vertebrae while maintaining a compressive load on the spinal implant. In some embodiments, three or more plates may be coupled together to form an adjustable-length spinal compression plate that spans two or more vertebral levels.

Plates of a spinal plate system may be curved to maintain a lordotic curvature of a human spine during compression of the spinal plate system. Plates may be provided with preformed curvatures to accommodate lordotic and/or radial vertebrae curvature. In some embodiments, a plate of a spinal compression plate may have one or more grooves to facilitate bending of the spinal compression plate to achieve a desired lordotic curvature.

Plates of a spinal plate system may be available in various sizes. The size of a plate utilized may depend on the number of vertebrae to be immobilized and/or the size of a patient. Plates may have an anterior side, a posterior side, and two ends. A spinal plate system may be coupled to vertebrae using one or more openings through the plates. Openings may be located at various positions alone the plate. A spinal plate system may have a center opening. An opening in a spinal compression plate may have a regular or an irregular shape. An opening in a spinal compression plate may be substantially circular or elongated. In some embodiments, a portion of a plate may form a wall of an opening. Alternatively, a liner, a cover, and/or a coating may form a wall of an opening.

Plates of a spinal plate system may be coupled together using coupling mechanisms to form a spinal compression plate. A coupling mechanism may include one or more coupling members and one or more coupling cavities. A coupling mechanism may include mating slots and extensions that allow movement of a plate of a spinal compression plate relative to another plate of the spinal compression plate. In some embodiments, a portion of a first plate may overlay a portion of a second plate. In some embodiments, one or more mating surfaces of plates of a spinal compression plate may have friction texturing. Plates may be coupled so that the plates can move in a longitudinal direction during use. A spinal compression plate may be compressed along a longitudinal axis during use. Movement of the plates may be restricted by the size of a coupling cavity.

In some embodiments, a spinal compression plate may compress longitudinally during use; however, the spinal compression plate may be inhibited from expanding longitudinally during use. A movement mechanism may inhibit expansion during use. In some embodiments, a movement mechanism may include one or more protrusions on the spinal compression plate. Protrusions may be positioned on surfaces of the plates that normally contact each other. Some embodiments include a protrusion on a first plate that engages one or more protrusions (e.g., serrations) on a second plate to maintain a distance between the vertebrae after compression. In some embodiments, at least a portion of a serrated surface of a movement mechanism may be curved to increase an area of the movement mechanism and thus enhance stability of a spinal compression plate.

A probe may be inserted into an opening in a spinal compression plate to release a movement mechanism (e.g., a ratcheting system) to allow expansion of the spinal compression plate. In an embodiment, an opening in a spinal compression plate may be used for monitoring the amount of compression of a spinal compression plate in a patient after insertion of the spinal compression plate. When the spinal compression plate compresses, a portion of a first plate may extend into an opening in the second plate. The position of the portion of the first plate relative to the opening in the second plate may be monitored using x-ray imaging to determine the amount of compression of the spinal compression plate.

Some spinal plate systems may include an engagement mechanism that inhibits separation of a first plate from a second plate of the spinal compression plate. An engagement mechanism may inhibit separation of the plates while allowing the plates to adjust for lordotic alignment as the spinal compression plate is compressed. In some embodiments, an engagement mechanism may include a protruding member of a first plate that engages serrations in a second plate.

In some embodiments, a spinal compression plate may freely compress and expand unencumbered by a movement mechanism. In some embodiments, a first plate may not include protrusions to engage protrusions on a second plate. In an embodiment, a second plate may not have protrusions to engage protrusions on a first plate. Compression and expansion of a spinal compression plate may allow the plate to accommodate natural vertebral movement. A coupling cavity may restrict the range of motion of a first plate relative to a second plate of a spinal compression plate and/or inhibit separation of the first plate from the second plate. In some embodiments, portions of the first plate that engage the second plate and/or portions of the second plate that engage the first plate, may be textured to alter frictional properties of the first plate relative to the second plate.

A spacer may set an initial separation between a first plate and a second plate of a spinal compression plate. The spacer may have an insertion end, an alignment portion, and a guidepost. The spacer may couple to a spinal compression plate. A fastener guide may be coupled to a guidepost of the spacer.

A positioner may be used to help position a spinal compression plate in a desired location in a patient. The position may have an engagement end, and alignment portion, and a guidepost. A fastener guide may be coupled to a guidepost of a positioner.

A plate insertion instrument may couple with a guide opening of a spinal compression plate to allow positioning of the spinal compression plate within a patient. In some embodiments, an engagement end of the plate insertion instrument may be press-fit into the guide opening of the spinal compression plate. In some embodiments, a plate insertion instrument may be attached to a portion of a spacer or positioner that is coupled to the spinal compression plate.

Spinal plate systems may be utilized in conjunction with implants and/or other medical devices. In certain instances, it may be beneficial for a spinal plate system to share at least some of the load experienced by a spinal plate system with a medical device. Bone growth may be increased around and through an implant that is carrying a load. Therefore, spinal plate systems may be designed to share a portion of the load from surrounding vertebrae with a spinal implant positioned between the vertebrae.

In some spinal plate system embodiments, a portion of a plate forms a wall of an opening. A recess may be positioned in a wall to engage a retainer that inhibits removal of a fastener from a plate. A recess may be biased to allow the fastener to enter a vertebra at a desired angle. Allowing a fastener to enter a spinal compression plate at an angle may facilitate establishment of a secure connection between the spinal compression plate and the vertebra. A recess may have a larger height than a height of the portion of a retainer that fits within the recess. The greater height of the recess may allow for some angulation adjustment of a fastener positioned through the retainer into a vertebra. In some embodiments, openings on a superior end of a spinal compression plate may allow for greater angulation of fasteners than openings on an inferior end of the spinal compression plate.

In some embodiments, a portion of an opening may have a spherically shaped contour to permit a fastener to be "obliquely angulated" relative to a plate. Herein, an "obliquely angulated" fastener refers to a fastener that may be positioned at a wide range of angles relative to a plate. In some embodiments, a range of angles may be from 0.degree. to about 20.degree. from an axis perpendicular to a plate.

A fastener may be secured in a plate using a retainer, such as a ring. A retainer may be positioned in an opening of a spinal compression plate. The opening of the spinal compression plate may be elongated to allow longitudinal movement of the retainer in the opening. An inner surface of a retainer may be shaped to accept head of a fastener while an outer surface of the retainer may be shaped to fit in an opening of the plate. In some embodiments, a serrated surface of a retainer may contact a serrated surface of an elongated opening of a plate to provide uni-directional longitudinal movement of the retainer in the opening. In some embodiments, a surface of a retainer may be textured (e.g., scored, peened, implanted with particles) to increase a frictional coefficient relative to a surface defining the opening so that motion of the retainer relative to the plate is inhibited but not prevented.

In certain embodiments, a fastener may include a head and a shank. An outer surface of a fastener head may be tapered such that an upper portion of the fastener head is larger than a lower portion of the fastener head. In some embodiments, a retainer, may have projections extending from an inner surface of the ring. The projections may engage a fastener head should the fastener move in a direction that would result in removal of the fastener from the opening. An outer surface of a retainer may include protrusions that engage a wall of an opening. In some embodiments, an inner surface of a retainer may include projections.

A retainer may have a gap that allows the retainer to radially expand and/or contract. A retainer may engage a fastener to inhibit backout of the fastener from a plate. Engaging a retainer with a fastener may inhibit a fastener head from rising above an upper, surface of the plate even if the fastener loosens in the bone. Retaining a fastener below the upper surface of a plate may inhibit contact of adjacent tissue with the fastener and/or fastener head during use. Damage of adjacent tissue may be minimized or eliminated by inhibiting contact of adjacent tissue with the fastener and/or fastener head during use.

In some embodiments, a retainer may be positioned in an opening of a spinal compression plate prior to surgical insertion of the compression plate in a patient. A spinal compression plate may be positioned adjacent to a portion of the spine that requires spinal fixation. Holes may be drilled, tapped, and/or otherwise formed in a portion of a vertebra underlying each opening. Fasteners may be inserted through the openings and into the holes. Fastener heads may be positioned in the openings so that retainers surround at least a portion of the fastener heads. Advantageously, a fastener may be held within the opening by a retainer. A spinal compression plate with a pre-positioned retainer may reduce concerns about positioning and/or dropping retainers during surgery.

BRIEF DESCRIPTION OF THE DRAWINGS

Advantages of the present invention will become apparent to those skilled in the alit with the benefit of the following detailed description and upon reference to the accompanying drawings in which:

FIG. 12 depicts a top view of the spinal compression plate shown in FIG. 11.

FIG. 13 depicts a top view of an embodiment of a spinal compression plate shown in an expanded position.

Figure 1:
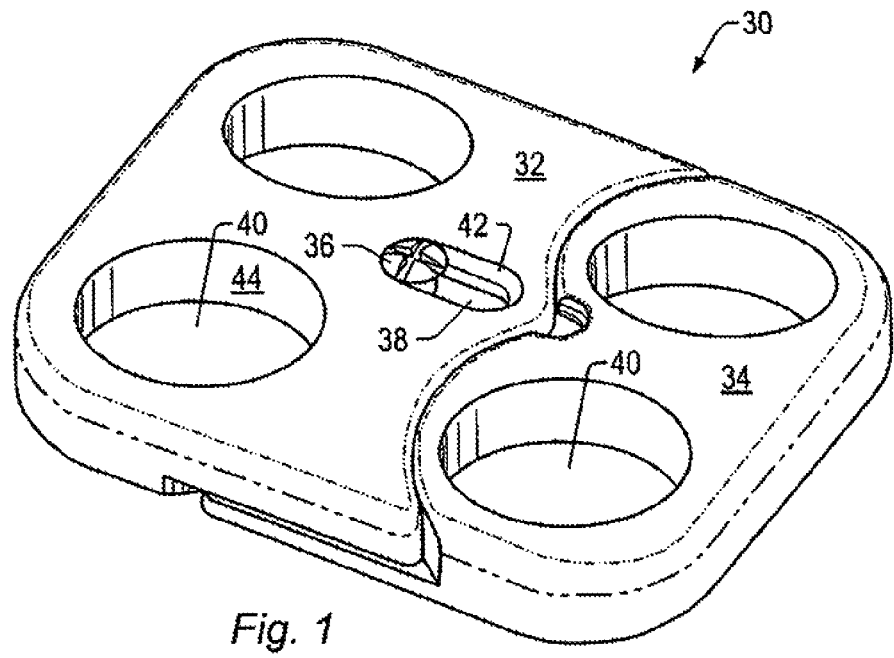
FIG. 1 depicts a perspective view of an embodiment of a spinal compression plate.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF EMBODIMENTS

A spinal plate system may be used to stabilize a portion of a spine. A spinal plate system may include a spinal compression plate and fasteners that couple the spinal compression plate to vertebrae. Components of a spinal plate system may include materials such as, but not limited to, stainless steel, titanium, titanium alloys, ceramics, and/or polymers. Some components of a spinal plate system may be made of materials that may be autoclaved and/or chemically sterilized. Some components of a spinal plate system may be formed of materials unable to be autoclaved and/or chemically sterilized. Components unable to be autoclaved and/or chemically sterilized may be made of sterile materials and placed in working relation to other sterile components during assembly of a spinal plate system.

Spinal plate systems may typically be used to correct problems in lumbar and cervical portions of a spine resulting from injury and/or disease. For example, a spinal plate system may be implanted anterior to a spine to maintain distraction between adjacent vertebral bodies in a cervical portion of the spine. A spinal compression plate of a spinal plate system may provide stability to one or more vertebral levels. A spinal compression plate may also facilitate bone fusion (e.g., spinal fusion). In some embodiments, a spinal compression plate may be used in conjunction with a spinal implant inserted in an intervertebral space between vertebrae. Spinal compression plates may accommodate settling and/or subsidence of a vertebra or vertebrae. Spinal compression plates may allow stress to be applied to a spinal implant. Stress applied to a spinal implant may promote bone growth between the spinal implant and the vertebrae.

Figure 2:
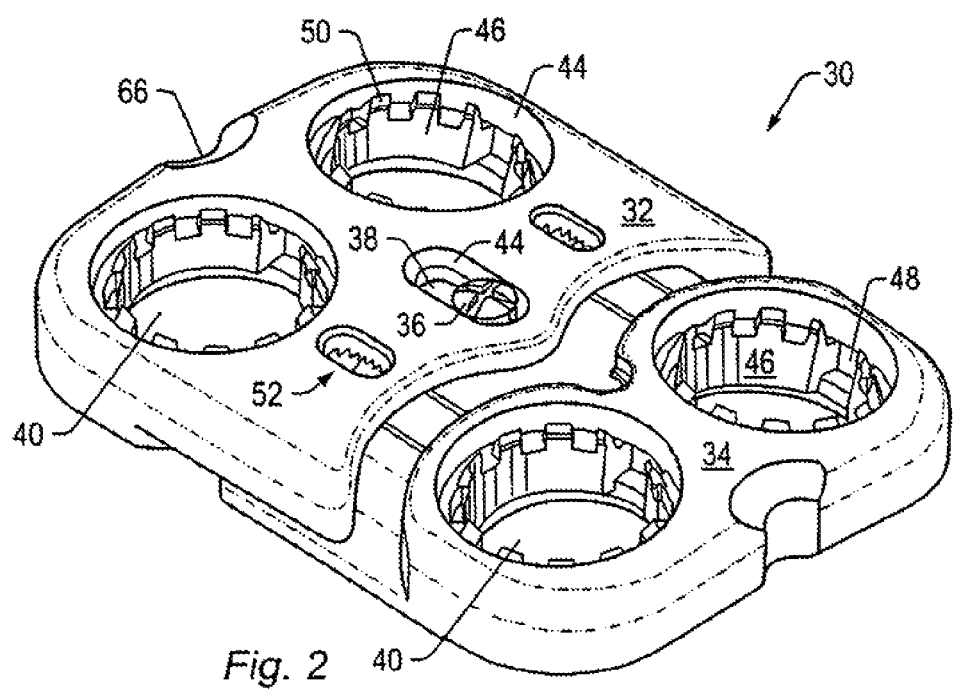
FIG. 2 depicts a perspective view of an embodiment of a spinal compression plate.

FIG. 1 and FIG. 2 depict embodiments of spinal compression plates. Spinal compression plates 30 may be used to provide stability to a single vertebral level. A single vertebral level includes a first vertebra and a second vertebra adjacent to the first vertebra. An intervertebral disc and/or a spinal implant may be located between the vertebrae. Spinal compression plate 30 may include first plate 32, second plate 34, coupling member 36, coupling cavity 38, and/or openings 40. In some embodiments, spinal compression plate 30 may also include one or more protrusions or spikes on a lower surface that penetrate vertebral surfaces when the spinal compression plate is installed. In some embodiments, first plate 32 and/or second plate 34 may include an opening to couple spinal compression plate 30 to an implant, bone graft, or other material positioned between vertebrae.

Coupling member 36 may join first plate 32 and second plate 34 while allowing movement of the first plate toward the second plate. In certain embodiments, coupling member 36 may be coupled to second plate 34. Coupling member 36 may be positioned in coupling cavity 38 of first plate 32. Coupling member 36 may have a head height that is reduced or eliminated by recessed surface 42 of coupling cavity 38 of first plate 32. In an embodiment, coupling member 36 is a pin positioned through coupling cavity 38 of first plate 32 into an opening of second plate 34. Coupling member 36 may be press-fit, welded, threaded, glued, or otherwise fixed to second plate 34. Coupling member 36 may inhibit separation of first plate 32 from second plate 34.

In some spinal compression plate embodiments, coupling member 36 may be positioned in first plate 32. Second plate 34 may have coupling cavity 38. As depicted in FIG. 1 and FIG. 2, coupling cavity 38 may be a closed slot. In other embodiments, coupling cavity 38 may be an open slot. As used herein, "slot" generally refers to an elongated opening of any size or shape, including an opening that deviates from an opening having a regular shape (such as a square or a circle) by elongation along at least one axis. Movement of coupling member 36 in coupling cavity 38 may allow longitudinal movement of first plate 32 relative to second plate 34. Coupling cavity 38 may include recessed surface 42. Recessed surface 42 may minimize or eliminate extension of coupling member 36 above spinal compression plate 30.

In some embodiments, a longitudinal length of coupling cavity 38 may limit motion of first plate 32 relative to second plate 34. In an embodiment, a portion of first plate 32 may contact a portion of second plate 34 to provide a boundary for a range of motion of the first plate relative to the second plate. FIG. 1 depicts spinal compression plate 30 in a fully compressed position. FIG. 2 depicts spinal compression plate 30 in an expanded position. In some embodiments, first plate 32 may be able to move about 8 mm relative to second plate 34. In some embodiments, first plate 32 may be able to move about 4 mm relative to second plate 34. In some embodiments, a range of motion of first plate 32 relative to second plate 34 may be smaller than about 4 mm or greater than about 8 mm.

Spinal compression plate 30 may include openings 40 extending through the plate. Fasteners inserted into openings 40 may couple spinal compression plate 30 to vertebrae. Portions of first plate 32 and second plate 34 may form walls 44 of openings 40. In some embodiments, walls 44 of openings 40 may be formed by liners, coatings, and/or coverings to modify frictional and/or other physical properties of the openings relative to fasteners inserted into the openings.

Openings 40 may be placed at various locations on first plate 32 and/or second plate 34. In some plate embodiments, openings 40 may be placed along midline axes of first plate 32 and second plate 34. Openings 40 may be symmetrically positioned about a midline axis of a plate near an end of the plate. In some embodiments, openings 40 may be positioned randomly or asymmetrically. In some embodiments, center openings may be positioned proximate a midpoint of spinal compression plate 30. A first center opening may be located in first plate 32. A second center opening, corresponding to the first center opening in first plate 32, may be located in second plate 34. The first center opening may at least partially align with the second center opening of assembled spinal compression plate 30. The first center opening and/or the second center opening may be elongated to accommodate movement of the first plate relative to the second plate.

As depicted in FIG. 2, retainer 46 may be positioned in opening 40 of spinal compression plate 30. In some embodiments, opening 40 may have an irregular shape to facilitate insertion of retainer 46 into the opening. Retainers 46 may include, but are not limited to, rings, c-rings, one or more crescents, annuli, cinctures, tabs, tangs, ridges, and/or shelves. In an embodiment, a portion of a retainer may be threaded. Retainer 46 may fit between wall 44 of opening 40 and a fastener. In some embodiments, wall 44 of opening 40 may engage retainer 46. In an embodiment, wall 44 of opening 40 may be smooth. In certain embodiments, wall 44 of opening 40 may be biased to engage a portion of a fastener used to couple spinal compression plate 30 to bone. Wall 44 of opening 40 may be curved and/or angled to allow angulation of a fastener into bone.

Wall 44 may have one or more indentions configured to engage a portion or portions of retainer 46. In some embodiments, one or more indentions may form recess 48. In some embodiments, a portion of retainer 46 may fit in recess 48. The shape of a portion of retainer 46 that fits in recess 48 may inhibit removal of the retainer from spinal compression plate 30. In some embodiments, retainer 46 may be free to rotate in opening 40.

In some embodiments, a wall of opening 40 defining recess 48 may have a spherical contour that corresponds to a contour of a spherical portion of a retainer. The spherical portion of the retainer may have a height that is less than a height of the recessed portion to allow for some polyaxial motion of the retainer when the retainer is positioned in recess 48. In some embodiments, the polyaxial motion allowed by recess 48 and a retainer may allow a fastener positioned in the retainer to be angled in a conic range of motion. In some embodiments, the range of motion of the fastener may be up to about 15° relative to a central axis normal to the center of an opening. In some embodiments, the range of motion of the fastener may be up to about 9° relative to a central axis normal to the center of the opening. In some embodiments, the range of motion of the fastener may be tip to about 3° relative to a central axis normal to the center of the opening. Larger or smaller ranges of motion may be accommodated by controlling the difference between the height of the recess and the height of the spherical portion of the retainer that resides in recess.

Retainer 46 may inhibit backout of a fastener from opening 40. In an embodiment, retainer 46 is a ring positioned in opening 40. Shape of the ring and the shape of the opening may inhibit removal of the ring from the opening.

Retainer 46 may include projections 50. Projections 50 of retainer 46 may deflect outward when a head of a fastener is inserted into the retainer during coupling of spinal compression plate 30 to a vertebra. After a portion of a fastener head passes projections 50, the projections may contract so that the projections extend over a portion of the head of the fastener. When a fastener is fully inserted into a vertebra, projections 50 may extend over a portion of a head of the fastener that is positioned in an opening of a spinal compression plate. Should the fastener move in a direction out of the opening of the spinal compression plate, a portion of the fastener head may contact projections 50 of retainer 46 that extend over the fastener head. Because the shape of retainer 46 inhibits removal of the retainer from the opening, contact of the fastener with projections 50 will inhibit removal of the fastener from the opening.

Retainer 46 may engage a head of a fastener without the retainer binding to spinal compression plate 30. Engagement of the fastener and retainer 46 may allow the fastener and retainer combination to pull spinal compression plate 30 against the vertebra. In some embodiments, fastener head may expand retainer 46 against wall 44 of opening 40 after the fastener and retainer combination pulls the spinal compression plate against the vertebra.

In some spinal compression plate embodiments, first plate 32 may move freely toward and away from second plate 34. In some embodiments, a uni-directional movement mechanism may limit movement of first plate 32 toward second plate 34. FIG. 2 depicts a spinal compression plate embodiment with a ratcheting mechanism as a uni-directional movement mechanism. Movement mechanism 52 may limit the direction that first plate 32 moves relative to second plate 34 (i.e., movement of the first plate may be uni-directional). In an embodiment, movement mechanism 52 may inhibit the motion of first plate 32 relative to second plate 34 until a desired load is applied to spinal compression plate 30. Inhibiting the motion of first plate 32 relative to second plate 34 until a desired load is applied to spinal compression plate 30 may accommodate normal motion of a patient without altering a distance between the first and second plates. First plate 32 may move closer to second plate 34 when adjacent vertebrae move closer together. In some embodiments, movement mechanism 52 may accommodate settling and/or subsidence of vertebrae after insertion of a spinal compression plate into a patient.

In an embodiment, first plate 32 may include serrations. Second plate 34 may include a protrusion that fits in serrations of first plate 32. In some embodiments, second plate 34 may include serrations and first plate 32 may include a protrusion that fits in the serrations. The serrations may have an equilateral shape to allow movement of first plate 32 toward or away from second plate 34. In some embodiments, serration shape may facilitate movement of first plate 32 toward second plate 34. In some embodiments, serration shape may inhibit movement of first plate 32 away from second plate 34.

Figure 3:
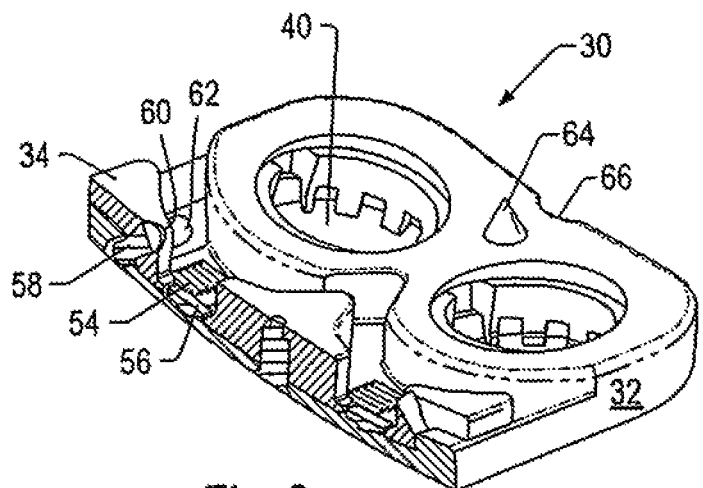
FIG. 3 depicts a perspective cross-sectional view of a posterior side of a spinal compression plate.

FIG. 3 depicts a portion of an embodiment of spinal compression plate 30. A lower surface of first plate 32 may include serrations 54. Protrusion 56 of second plate 34 may extend into a space between serrations 54. Protrusion 56 may be located on a flexible arm. In some spinal compression plate embodiments, second plate 34 may include two or more protrusions 56 that engage serrations 54. Orientation of serrations 54 and protrusion 56 may allow uni-directional movement of first plate 32 toward second plate 34 (i.e., inhibiting movement of the first plate away from the second plate). Serrations 54 and protrusion 56 may be sized so that first plate 32 is not able to move toward second plate 34 until a desired compressive load is applied to spinal compression plate 30.

In some spinal compression plate embodiments, an engagement mechanism may limit a range of motion of first plate 32 relative to second plate 34. An engagement mechanism may include one or more protruding members 58 that extend through one or more openings 60 in second plate 34 into one or more chambers 62 of first plate 32. Protruding members 58 may include, but are not limited to, pins, rivets, and/or screws. Protruding members 58 may inhibit rotation of first plate 32 relative to second plate 34. In addition, protruding members 58 may provide one or more boundaries that limit a range of motion of first plate 32 relative to second plate 34. Chamber 62 may be curved and/or angled to accommodate curvature of spinal compression plate 30. In some embodiments, protruding member 58 may be a guide pin. A guide pin may enter chamber 62 and facilitate coupling of first plate 32 and second plate 34. Protruding member 58 may enhance stability of spinal compression plate 30.

In some embodiments, spinal compression plate 30 may include one or more protrusions 64. Protrusions 64 may be securely positioned in openings of first plate 32 and/or second plate 34. Protrusions 64 may be, but are not limited to being, press-fit, welded glued, and/or otherwise affixed to first plate 32 and/or second plate 34. Protrusions 64 may be driven into a vertebra to initially couple spinal compression plate 30 to the vertebra. After spinal compression plate 30 is initially coupled to the vertebra, the spinal compression plate may be more securely coupled to the vertebra with fasteners.

In some spinal compression plate embodiments, first plate 32 and/or second plate 34 may include indentions 66, as shown in FIG. 2 and FIG. 3. Indentions 66 may facilitate proper positioning of first plate 32 and second plate 34 during an insertion procedure. Indentions 66 may provide an engagement surface for a spacer that sets a position of first plate 32 relative to second plate 34 (i.e., establishes a length of the spinal compression plate) prior to and/or during insertion of spinal compression plate 30.

Figure 4:
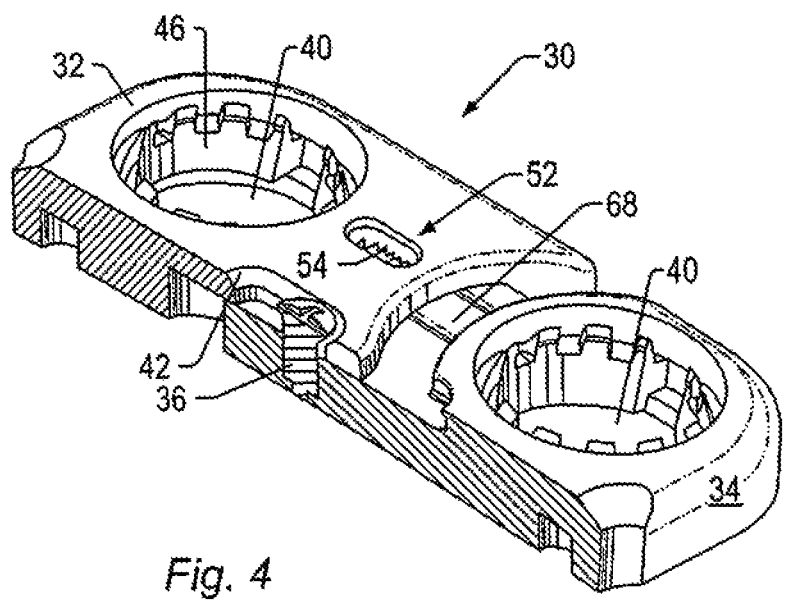
FIG. 4 depicts a perspective cross-sectional view of a spinal compression plate in an expanded position.

FIG. 4 depicts a cross section of a perspective view of an embodiment of spinal compression plate 30. First plate 32 and second plate 34 may have retainers 46 positioned in openings 40. Movement of first plate 32 relative to second plate 34 may be limited by movement mechanism 52. Movement mechanism 52 may include a protrusion on flexible arm 68 of second plate 34 that engages serrations 54 on first plate 32.

Figure 5:
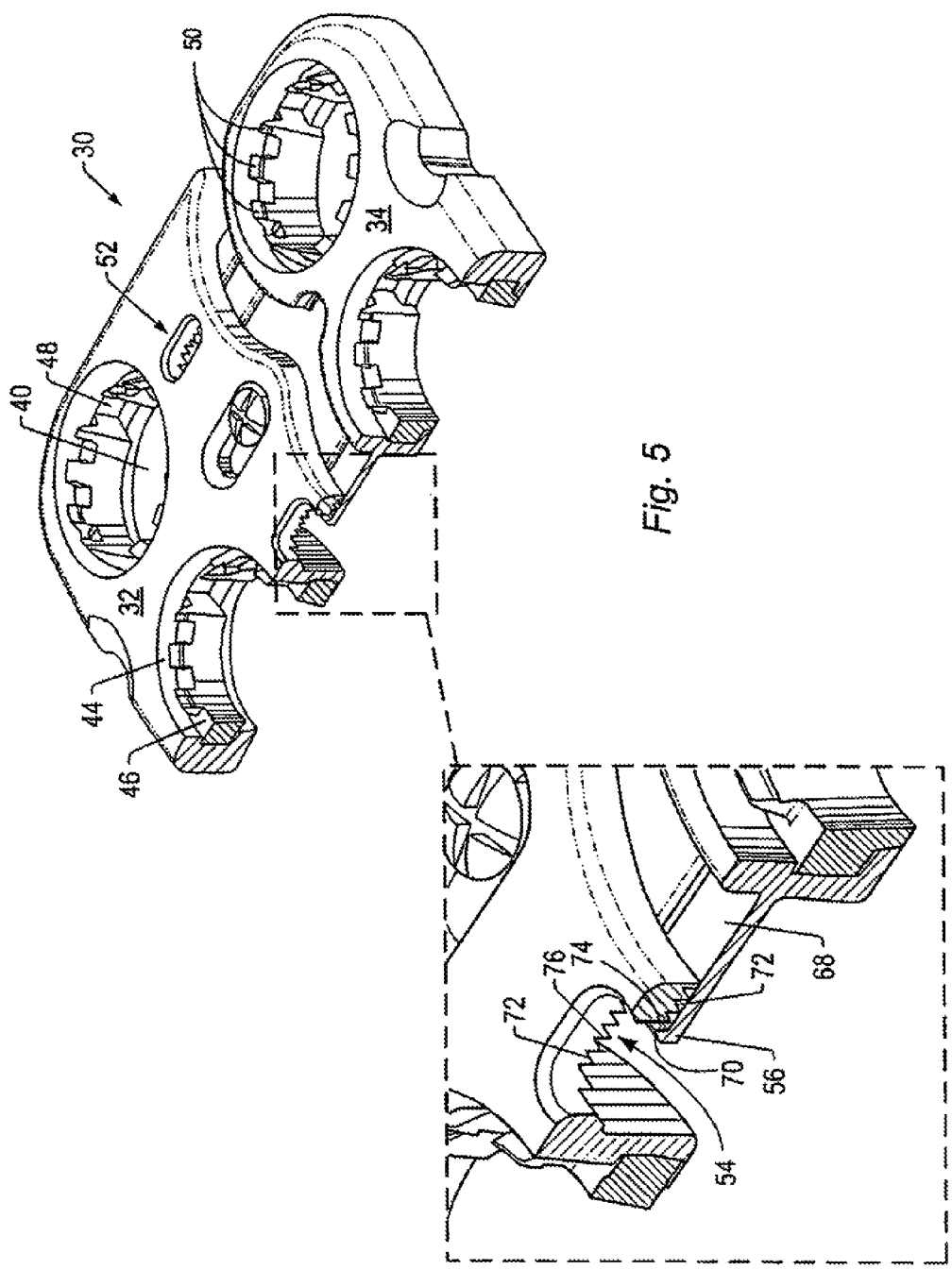
FIG. 5 depicts a perspective cross-sectional view of a spinal compression plate, including an inset view showing a magnified portion of spinal plates.

FIG. 5 depicts a cross section of a perspective view of spinal compression plate 30, including a detailed view of a portion of the spinal compression plate. Movement mechanism 52 of spinal compression plate 30 may include protrusion 56 that extends from flexible arm 68 of second plate 34 and engages serrations 54 on a lower surface of first plate 32. Protrusion 56 (e.g., a tooth) and serrations 54 allow relative movement of first plate 32 and second plate 34 toward each other.

In some embodiments, protrusion 56 may have first angled surface 70 that engages angled surface 72 of serrations 54. Contact of angled surface 70 of protrusion 56 with angled surface 72 of serrations 54 may allow second plate 34 to move toward first plate 32. Protrusion 56 may also include straight surface 74 that engages straight surface 76 of a tooth of serrations 54. If force is applied to second plate 34 to move the second plate away from first plate 32, straight surface 74 of protrusion 56 may contact straight surface 76 of a tooth of serrations 54. In some embodiments, contact of protrusions 56 and serrations 54 may inhibit movement of second plate 34 away from first plate 32. When coupled to vertebrae, the relative movement of first plate 32 and second plate 34 may accommodate settling and/or subsidence of the vertebrae after insertion of spinal compression plate 30.

Figure 6:
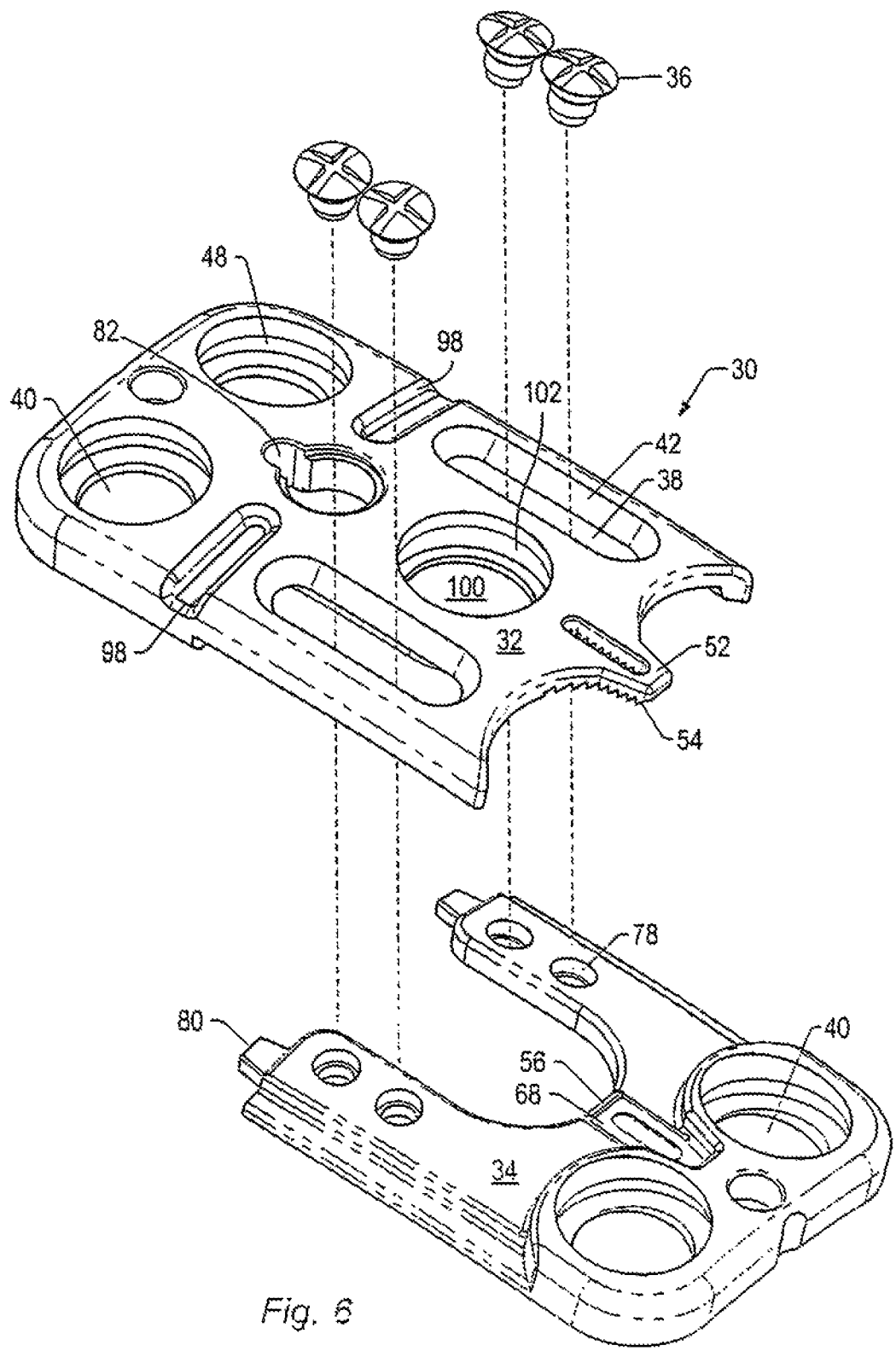
FIG. 6 depicts an exploded view of an embodiment of a spinal compression plate.

FIG. 6 depicts an exploded view of an embodiment of spinal compression plate 30. Spinal compression plate 30 may include first plate 32 and second plate 34. First plate 32 and second plate 34 may be coupled together with coupling members 36 in coupling cavities 38 proximate sides of the first plate. Coupling cavities 38 proximate sides of first plate 32 may inhibit rotation and/or torquing of spinal compression plate 30 during use. Coupling cavity 38 may have recessed surface 42. One or more coupling members 36 may be used in each coupling cavity 38. In an embodiment, coupling cavity 38 is tapered. During assembly of spinal compression plate 30, coupling member 36 may be placed through coupling cavity 38 into coupling member opening 78. Coupling member 36 may be attached to coupling member opening 78 on second plate 34 using a weld, an adhesive, threading, and/or a frictional lock. As spinal compression plate 30 is compressed, tab 80 on second plate 34 may enter an undercut portion of first plate 32.

In the spinal compression plate embodiment of FIG. 6, spinal compression plate 30 may include movement mechanism 52. First plate 32 may have serrations 54 that engage protrusion 56 on flexible arm 68 of second plate 34. A movement mechanism may inhibit first plate 32 from moving away from second plate 34. In some spinal compression plate embodiments, first plate 32 and second plate 34 may be able to move freely relative to each other. First plate 32 and/or second plate 34 may include one or more guide openings 82. Guide opening 82 may allow proper positioning of instrumentation (e.g., insertion instruments, drills, and/or tap guides) during an insertion procedure.

Figures 7, 8:
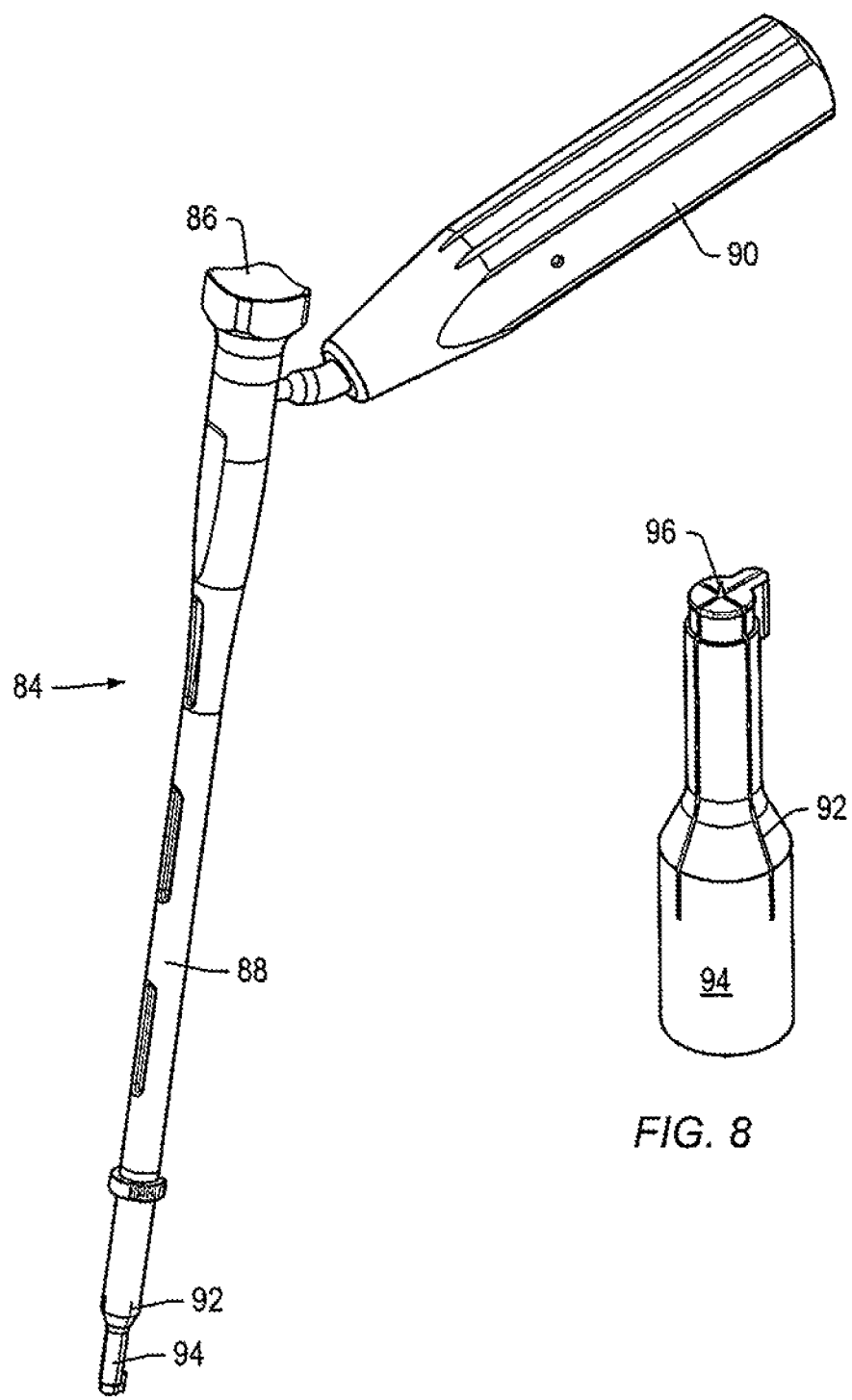
FIG. 7 depicts an embodiment of a plate insertion instrument.
FIG. 8 depicts an engagement end of the plate insertion instrument shown in FIG. 7.

FIG. 7 depicts an embodiment of a plate insertion instrument that may be positioned in a guide opening. Plate insertion instrument 84 may include actuator surface 86, shaft 88, handle 90, slots 92, and engagement end 94. Engagement end 94 may fit in an opening (e.g., a guide opening) of a spinal compression plate. Slots 92 may be compressed when engagement end 94 is placed in an opening of a spinal compression plate to form a press-fit engagement between plate insertion instrument 84 and the spinal compression plate.

Handle 90 of insertion instrument 84 may extend away from shaft 88 of the insertion instrument. Handle 90 may allow a spinal compression plate to be properly positioned on vertebrae within a surgical opening. When a spinal compression plate is properly positioned, a user may push or strike actuator surface 86 to drive at least one spike of the spinal compression plate into at least one vertebra.

In some embodiments, a tip of an engagement end of a plate insertion instrument may include a spike. FIG. 8 depicts spike 96 on engagement end 94 of a plate insertion instrument. Spike 96 may facilitate temporary placement of a spinal compression plate during insertion. A press-fit connection between a spinal compression plate and plate insertion instrument 84 may be removed by moving the plate insertion instrument away from the spinal compression plate.

In some procedures, a tamp or other instrument may be held against a spinal compression plate to ensure that a press-fit connection between the spinal compression plate and an insertion instrument is removed when the insertion instrument is lifted from the spinal compression plate. A guide opening of a spinal compression plate may be used as a viewport to observe an implant positioned between adjacent vertebrae. A guide opening may help to reduce a weight of a spinal compression plate. In some embodiments, a fastener may be positioned through a guide opening to couple a spinal compression plate to a spinal implant, a vertebra displacement construct, or other device to be positioned between vertebrae.

In some embodiments, a plate bender may be provided in an instrumentation set to allow a spinal compression plate to be bent to accommodate a lordotic angle of a patient. As shown in FIG. 6, first plate 32 of spinal compression plate 30 may include grooves 98. Grooves 98 may allow first plate 32 to be bent prior to fixation to a vertebra. Spinal compression plate 30 may be bent alone grooves 98 to conform the plate to a vertebra or vertebrae. In some embodiments, a second plate may include grooves that facilitate bending of the spinal compression plate.

In some embodiments, a spinal compression plate may be curved to correspond to a lordotic curvature and/or mediolateral curvature of a spine. Bending of a spinal compression plate may allow proper lordotic curvature of a spine to be maintained. Several spinal compression plates with different lordotic curvatures may be provided to a surgeon who will install a spinal compression plate in a patient. Spinal compression plates may have various widths, lengths, and/or curvatures. The surgeon may choose a spinal compression plate that will provide a desired lordotic curvature for the patient. Indicia may be etched or otherwise marked (e.g., color coded) on a spinal compression plate to indicate an amount of curvature in the plate. In some embodiments, spinal compression plates may be provided with lordotic angles from about 0° to about 18° in about 3° increments. For example, a spinal compression plate may have a length of about 28 mm, a maximum width of about 15 mm, and a 12° lordotic curvature.

A width of a spinal compression plate may affect intrusion of the spinal compression plate into surrounding tissue. In an embodiment, a spinal compression plate, may have a width less than about 40 mm. In some embodiments, a spinal compression plate may have a width less than about 35 mm. Larger or smaller widths may be used to accommodate specific needs. In certain embodiments, width of a spinal compression plate may vary along a midline axis of the spinal compression plate. Variance along a midline axis may reduce intrusion of a spinal compression plate into surrounding tissue, reduce the weight of the plate, and/or improve viewing of the intervertebral space during insertion. In some embodiments, openings may be formed in a spinal compression plate to reduce weight and/or increase visibility of a surgical site.

A height of a spinal compression plate may affect a profile of the spinal compression plate on the spine. In some embodiments, an average height of greater than about 6.0 mm may be used. In other embodiments, spinal compression plates may have an average height of less than about 6.0 mm. For example, a height of a spinal compression plate may be less than about 5.0 mm, less than about 3.5 mm, or less than about 2.7 mm. A height of a spinal compression plate may vary along a length and/or width of the spinal compression plate.

Some spinal compression plate embodiments may be curved to accommodate radial curvature of vertebrae. Spinal compression plates may be provided with varying amounts of radial curvature. For example, spinal compression plates may be provided in large, medium and small radial curvature sizes. An indication of the radial curvature provided by a spinal compression plate may be etched or otherwise marked on the spinal compression plate.

As shown in FIG. 6, spinal compression plate 30 may include at least one center opening 100 positioned proximate a center of the spinal compression plate. In some embodiments, center opening 100 may be positioned proximate a center of first plate 32 and/or second plate 34. A center opening in first plate 32 may align or partially align with a center opening in second plate 34. Center openings may include, but are not limited to substantially oval, circular, square, and rectangular shapes, oblong shapes, irregular shapes, and open or closed slots. An oblong or elongated opening may be defined as an opening that deviates from an opening having a regular shape (such as a square or circle) by elongation along at least one axis. In some embodiments, a first axis of center opening 100 may be larger than a second axis of the center opening, allowing a large center opening without significant loss in structural strength of spinal compression plate 30.

In certain embodiments, center opening 100 may have recess 102. A back portion of a retainer may fit in recess 102 of center opening 100. Shapes of recess 102, of center opening 100 and of a retainer positioned in the center opening may inhibit removal of the retainer from spinal compression plate 30. The retainer may be free to rotate in recess 102. In some embodiments, center opening 100 may be elongated. A retainer in an elongated or oblong center opening may slide freely in a longitudinal direction. The retainer may inhibit backout of a fastener positioned in center opening. In an embodiment in which a spinal compression plate spans more than two vertebrae, a fastener positioned in center opening 100 of the spinal compression plate may couple the spinal compression plate to a vertebra or a spinal implant.

Figure 9:
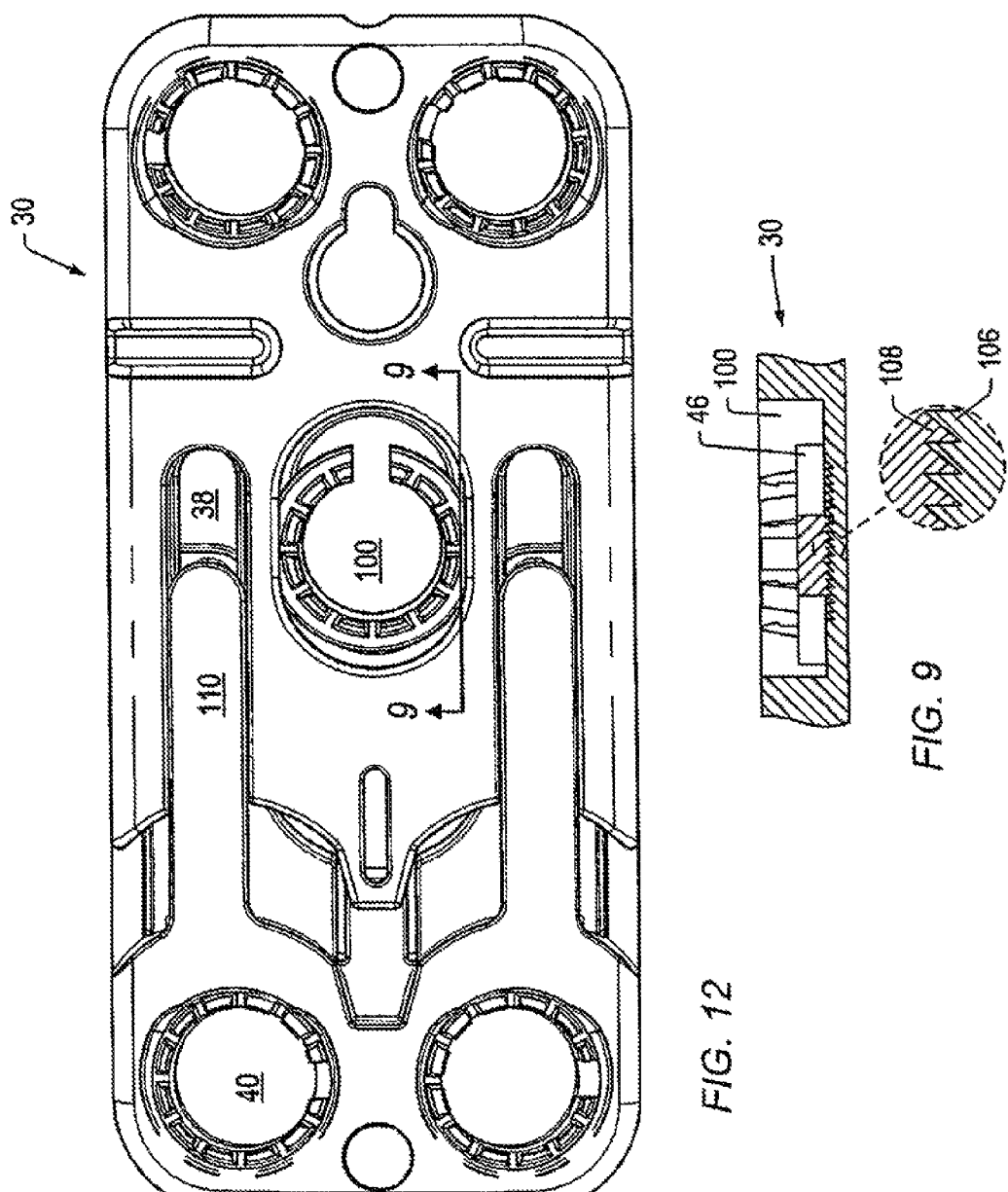
FIG. 9 depicts a cross-sectional view of a serrated retainer.

In certain embodiments, a retainer may have restricted movement in an opening of a spinal compression plate. FIG. 9 depicts a cross-sectional view of serrated retainer 46 taken essentially along line 9-9 of spinal compression plate 30 in FIG. 12. Serrations 106 on a surface of center opening 100 may engage serrations 108 on a bottom surface of retainer 46. Engagement of serrations 106, 108 may restrict longitudinal movement of retainer 46 in opening 100. In some embodiments, longitudinal movement of retainer 46 may be uni-directional. In some embodiments, movement of retainer 46 may occur only after a compressive load on a spinal compression plate reaches a certain threshold.

Figure 10:
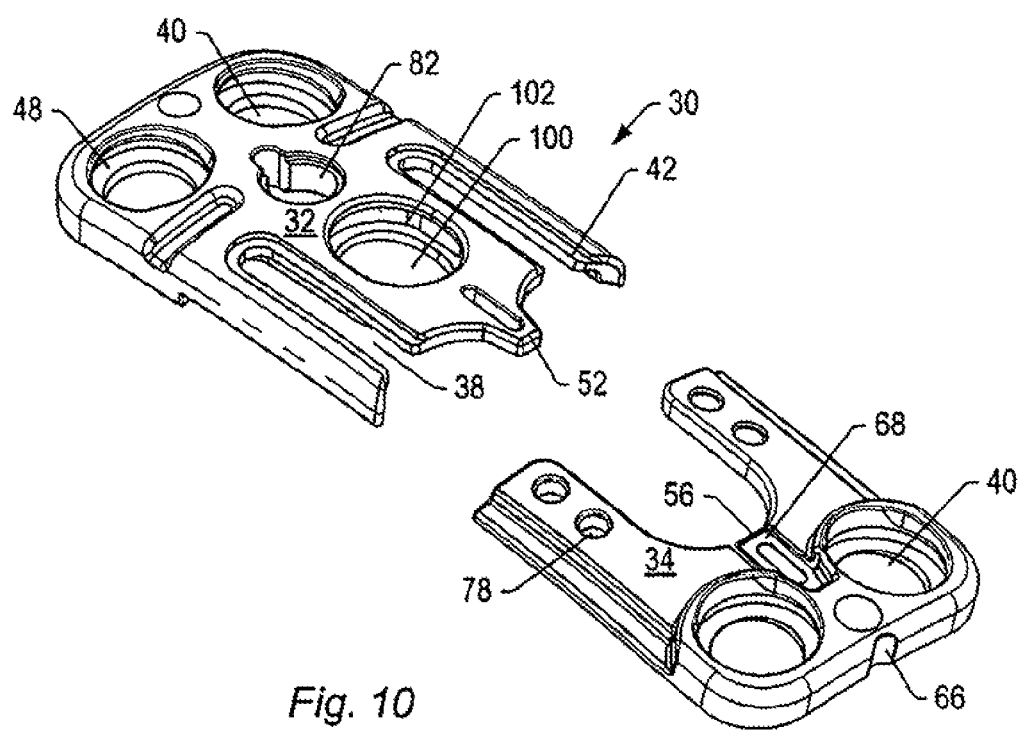
FIG. 10 depicts a perspective view of an embodiment of spinal compression plate.

FIG. 10 depicts a perspective view of an embodiment of spinal compression plate 30. Spinal compression plate 30 may include first plate 32 and second plate 34. Second plate 34 may be similar to a second plate in a spinal compression plate with uni-directional movement, shown in FIG. 6. Without serrations on movement mechanism 52 to engage protrusion 56 on flexible arm 68 of second plate 34, first plate 32 may freely move toward and/or away from the second plate to accommodate motion of vertebrae. In some spinal compression plate embodiments, movement mechanism 52 on first plate 32 may have serrations, but second plate 34 may not have flexible arm 68 and/or protrusion 56. Movement of first plate 32 relative to second plate 34 may be limited by coupling cavity 38 and coupling member opening 78. A coupling member positioned in coupling cavity 38 may define a minimum and/or maximum separation between first plate 32 and second plate 34 while inhibiting separation of first plate 32 from second plate 34 and/or rotation of the first plate relative to the second plate.

Figure 11:
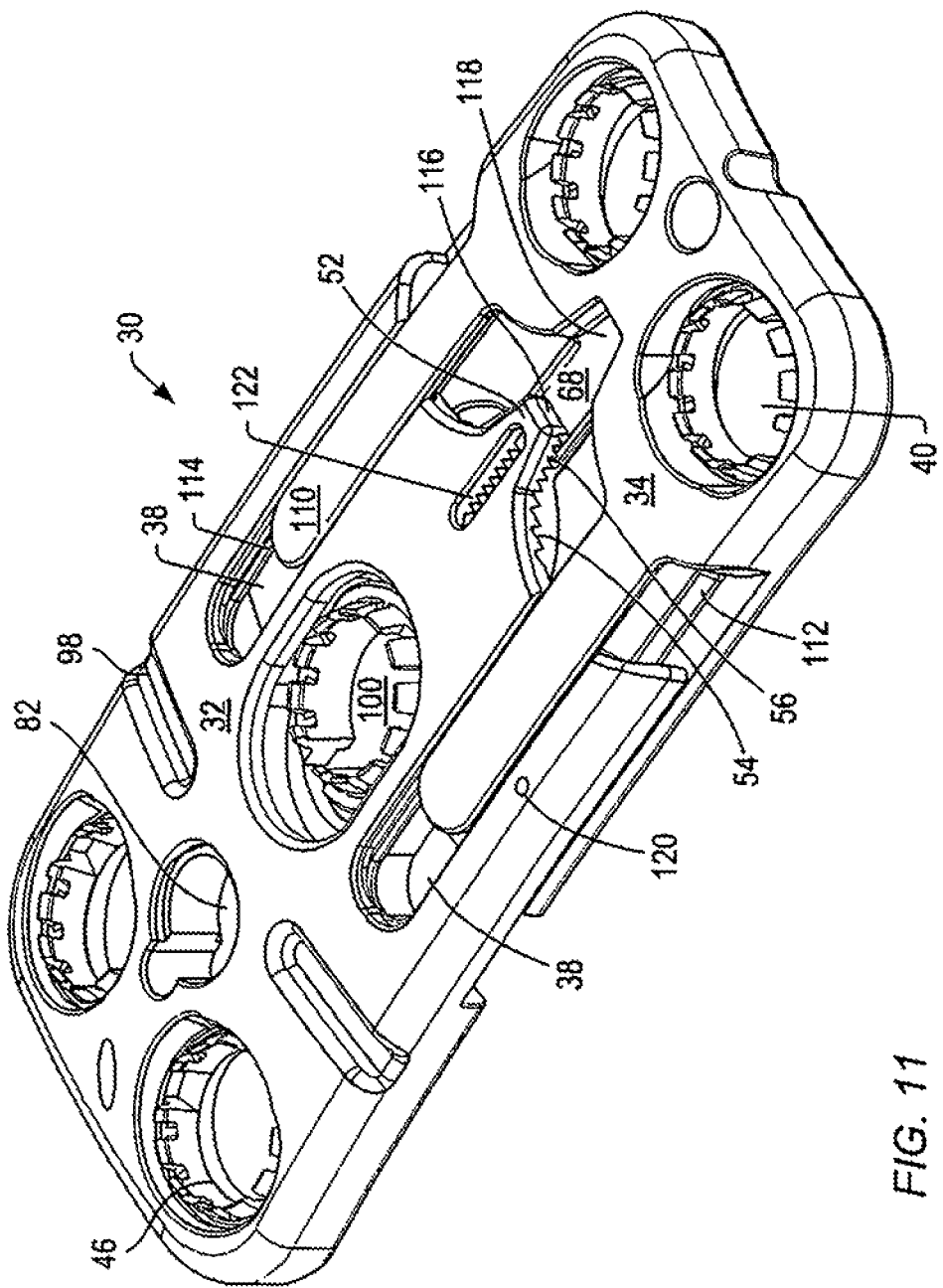
FIG. 11 depicts a perspective view of an embodiment of a spinal compression plate.

A spinal compression plate embodiment may include an internal tongue and groove, a pin in slot, and/or other types of connections between first plate 32 and second plate 34 to inhibit rotation of the first plate relative to the second plate. FIG. 11 depicts a perspective view of spinal compression plate 30 with tongue and groove connections between first plate 32 and second plate 34. Extensions 110 of second plate 34 may fit securely in open slot coupling cavities 38 of first plate 32 to form spinal compression plate 30. As used herein, an "extension" generally refers to an elongated portion of a body. An elongated portion of a body may be defined as a portion of a body that deviates from a regular shape (such as a square or circle) by elongation along at least one axis. In some embodiments, a first axis of an extension may be larger than a second axis of the extension.

Extensions 110 may have stepped portions 112 that mate with stepped portions 114 of coupling cavities 38. Stepped portions 112, 114 may enhance stability of spinal compression plate 30 by inhibiting torque moments applied to first plate 32 and/or second plate 34 during expansion or compression of the spinal compression plate. In some embodiments, stepped portions 112, 114 may be textured with a friction texturing to reduce slippage between first plate 32 and second plate 34. The friction texturing may be, but is not limited to, scored surfaces, peened surfaces, and/or surfaces with particles implanted into the surfaces.

Spinal compression plate 30 may have movement mechanism 52 on first plate 32. In some embodiments, a lower surface of movement mechanism 52 may have serrations 54. Movement mechanism 52 may have extended portion 116 that fits in cavity 118 of second plate 34. An edge of extended portion 116 of movement mechanism 52 may be substantially flat. Sides of movement mechanism 52 may be curved to allow extended portion 116 to approach openings 40 of second plate 34. Extended portion 116 of movement mechanism 52 may increase a serrated surface area of the movement mechanism and thus enhance coupling stability between first plate 32 and second plate 34.

Protrusion 56 on an upper surface of flexible arm 68 of second plate 34 may engage serrations 54 on first plate 32 to provide uni-directional movement of the first plate toward second plate 34. In certain embodiments, a shape of serrations 54 may allow spinal compression plate 30 to compress and/or expand. In some spinal compression plate embodiments, movement mechanism 52 may not be serrated. In some spinal compression plate embodiments, second plate 34 may not have protrusion 56 and/or flexible arm 68. In certain spinal compression plate embodiments, cross pin 120 may extend from an upper surface of first plate 32 through stepped portion 114 of coupling cavity 38 into a longitudinal slot in stepped portion 112 of extension 110 of second plate 34. A length of the longitudinal slot in stepped portion 112 of extension 110 may limit a range of motion of first plate 32 relative to second plate 34.

Spinal compression plate 30 may have slot 122 in movement mechanism 52 of first plate 32. In some embodiments, protrusion 56 may be disengaged from serrations 54 by insertion of a tip of a probe (e.g., a screwdriver blade) in slot 122. A user may slide first plate 32 and second plate 34 apart while applying a slight pressure to flexible arm 68 of second plate 34. The probe may be removed from slot 122 (i.e., to release flexible arm 68) when a desired separation between first plate 32 and second plate 34 is achieved.

In some spinal compression plate embodiments, slot 122 may be used as a viewport to monitor compression of spinal compression plate 30 after a spinal stabilization procedure. A length of slot 122 may be a known distance (erg, 8 mm, 6 mm, 4 mm, or other length) so that a scale factor can be calculated for lengths determined from x-ray images taken of the spinal compression plate. When a maximum allowable compression distance of spinal compression plate is set using a spacer, an end of flexible arm 68 may be visible in slot. After installation of spinal compression plate is complete, an initial x-ray image of the installed spinal compression plate may be taken. Distance from the end of flexible arm 68 to an end of slot 122 may be determined from the x-ray image to provide a value for the initial separation distance. At a later time, another x-ray image may be taken. Distance from the end of flexible arm 68 to the end of slot 122 may be determined from the x-ray image to provide a second distance. The difference between the initial separation distance and the second distance measures the amount of compression of the spinal compression plate. Additional x-ray images may be taken at subsequent times to monitor the amount of compression as a function of time.

FIG. 12 depicts a top view of a spinal compression plate embodiment with first plate 32 and second plate 34 of spinal compression plate 30 coupled with mating open slot coupling cavities 38 and extensions 110. Spinal compression plate 30 has irregularly shaped openings 40 and elongated center opening 100. Irregularly shaped opening 40 may be configured to facilitate insertion of a retainer into the opening. In an embodiment, a portion of opening 40 may have a larger radius of curvature than another portion of the opening.

FIG. 13 depicts an expanded top view of an embodiment of a spinal compression plate that may be used to immobilize two vertebral levels. Multi-level spinal compression plate 30 may include two or more plates. In some embodiments, spinal compression plate 30 may include first plate 32, second plate 34, and third plate 124. Plates 32, 34, 124 may be coupled to vertebrae when using spinal compression plate 30 to stabilize a spine. Fasteners positioned in openings 40 of first plate 32, second plate 34, and third plate 124 may couple spinal compression plate 30 to vertebrae. First plate 32 and third plate 124 may be coupled to second plate 34 using coupling members 36 in coupling cavities 38. Portions of first plate 32 and third plate 124 may overlap portions of second plate 34. After insertion, spinal compression plate 30 may be compressed from an expanded form to accommodate vertebral settling and/or subsidence.

In some embodiments, spinal compression plate 30 may have one or more movement mechanisms to restrict movement between plates 32, 34, and 124. Serrations on a plate may engage one or more protrusions on another plate. In an embodiment, a movement mechanism may allow a spinal compression plate to compress and may restrict movement of the plates away from each other. In some embodiments, second plate 34 may have protrusions on opposing sides to engage first plate 32 and third plate 124. In an embodiment, first plate 32 may have serrations to engage a protrusion on second plate 34. Third plate 124 may not have serrations. First plate 32 may move only toward second plate 34, and third plate 124 may move toward and away from the second plate. In an embodiment, first plate 32, second plate 34, and third plate 124 may be allowed to compress or expand to accommodate movement of vertebrae.

Figure 14:
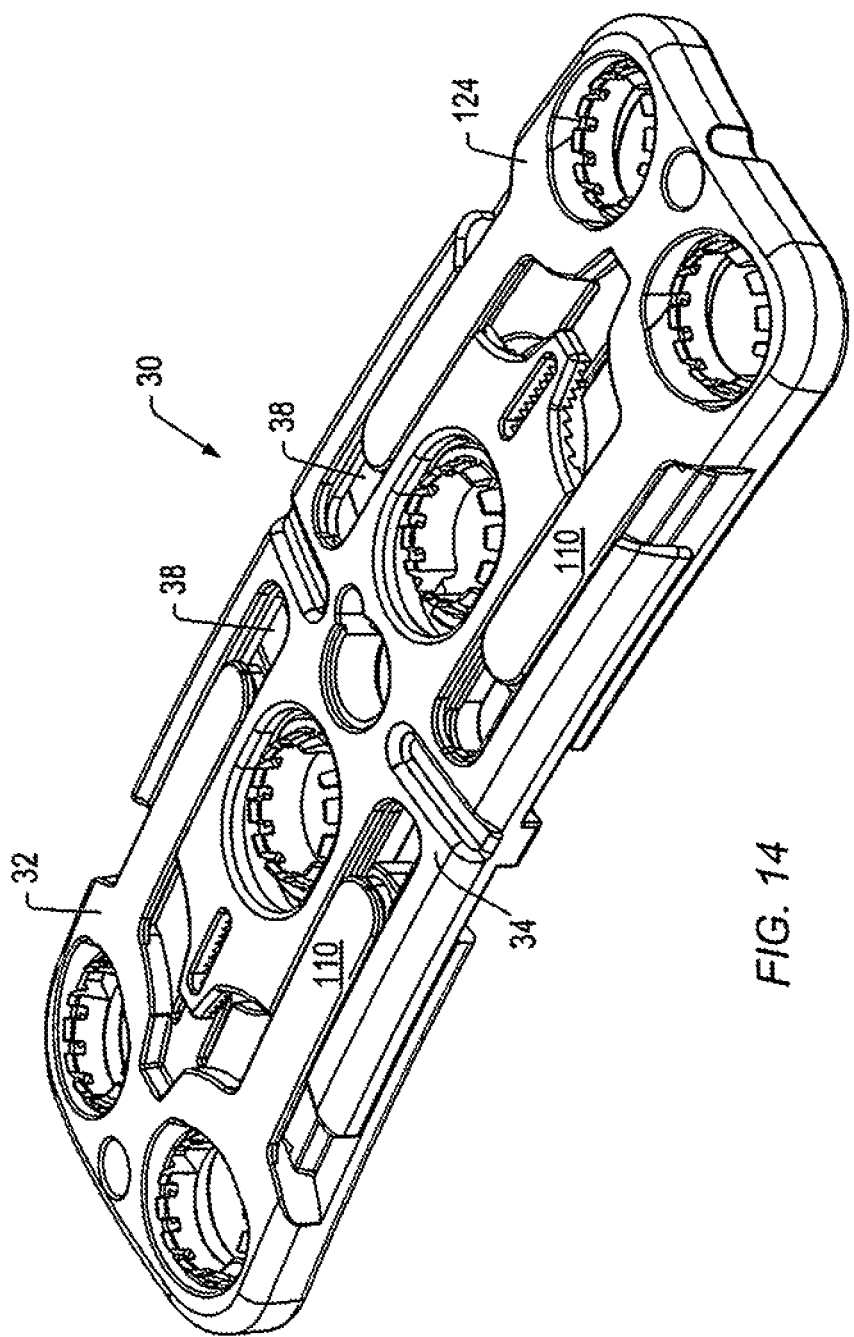
FIG. 14 depicts a perspective view of an embodiment of a multi-level spinal compression plate.

In certain embodiments, plates of a multi-level spinal compression plate may be coupled together without coupling members (e.g., with mating slots and extensions). FIG. 14 depicts uni-directional multi-level spinal compression plate 30 with first plate 32, second plate 34, and third plate 124. Multi-level spinal compression plate 30 may be used to span three vertebral levels. In other embodiments, multi-level spinal compression plates may be used to span four vertebral levels. Extensions 110 of first plate 32 and third plate 124 may fit securely in open slot coupling cavities 38. In some embodiments, plates of spinal compression plate 30 may move freely with respect to each other.

Figure 15:
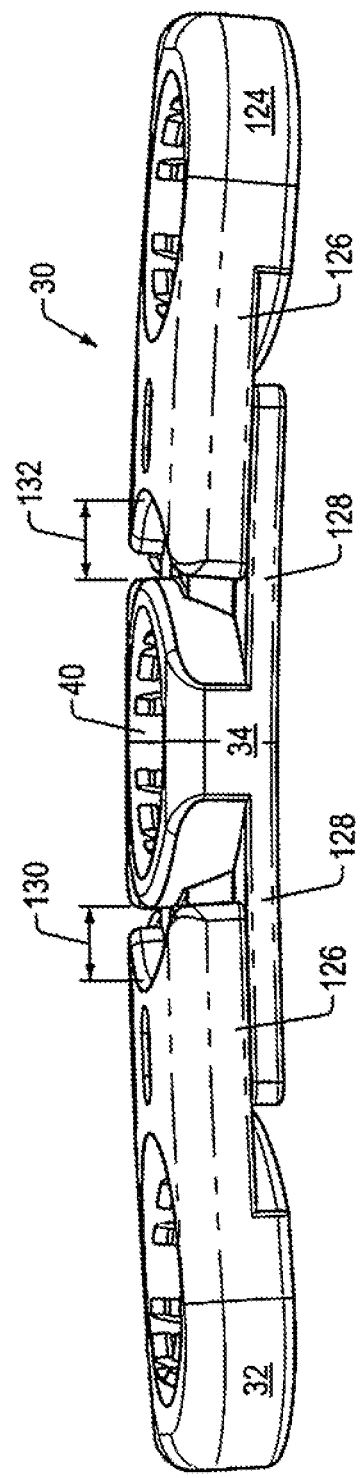
FIG. 15 depicts a side view of an embodiment of a spinal compression plate.

FIG. 15 depicts a side view of an embodiment of multi-level spinal compression plate 30. First plate 32 and third plate 124 may include overlay sections 126 that are shaped to conform to underlay sections 128 on second plate 34. Upper and lower surfaces of the plates may be curved to correspond to a desired lordotic curvature. Distance 130 indicates an initial separation between first plate 32 and second plate 34. Distance 132 indicates an initial separation between second plate 34 and third plate 124. A maximum compression of spinal compression plate 30 may be equal to the sum of distance 130 and distance 132.

Figure 16:
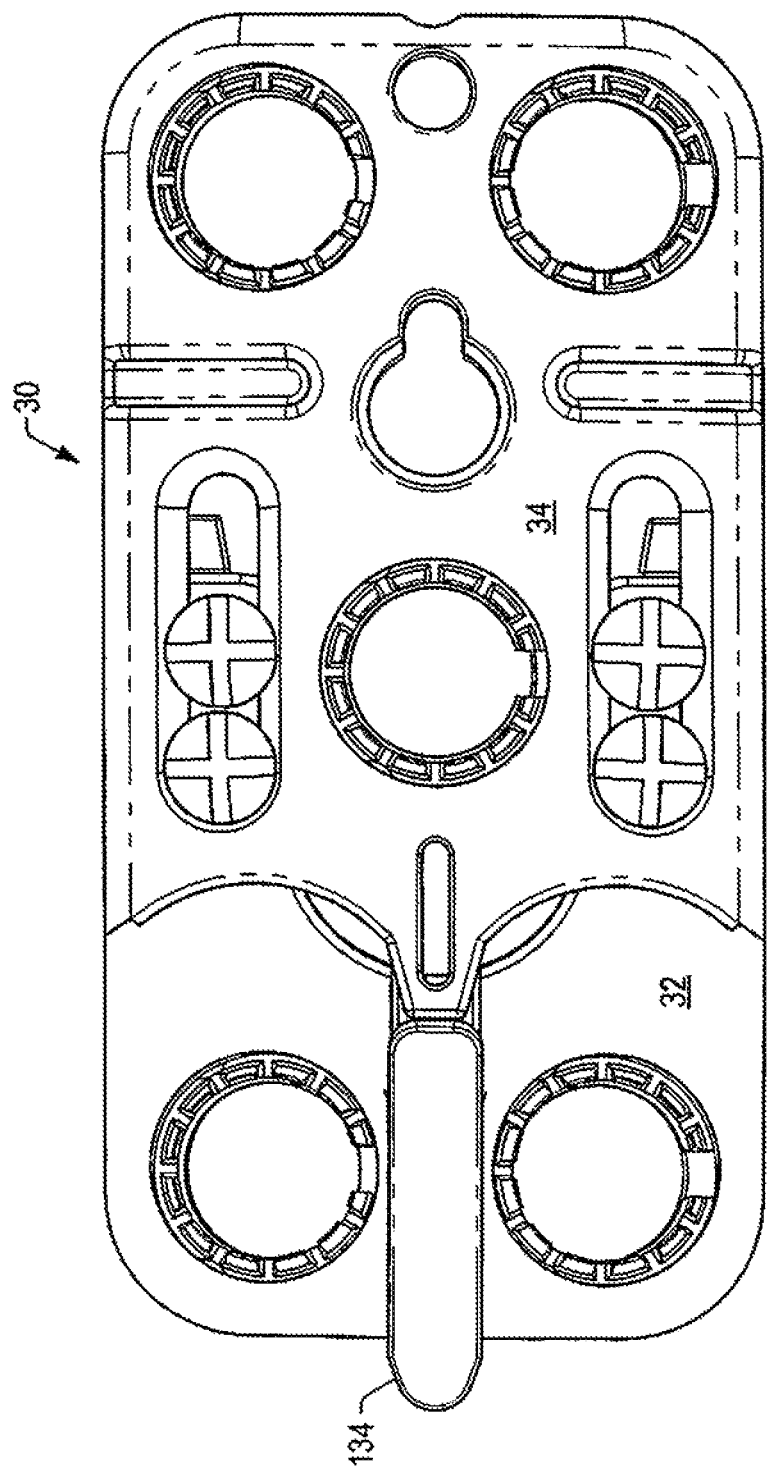
FIG. 16 depicts a top view of an embodiment of a spinal compression plate with a spacer.

FIG. 16 depicts an embodiment of spinal compression plate 30 with spacer 134. First plate 32 and second plate 34 may be positioned for a desired length of spinal compression plate 30 prior to insertion of the spinal compression plate in a patient. Spacer 134 may position first plate 32 relative to second plate 34 to establish an initial (i.e., maximum) separation distance between the first plate and the second plate. Spacer 134 may have a length that allows for an initial separation distance of about 8 mm. In some embodiments, spacer 134 may allow a pre-set initial separation of about 4 mm. Spacers 134 of various lengths may be included in an instrumentation set provided with spinal compression plate 30.

Figure 17:
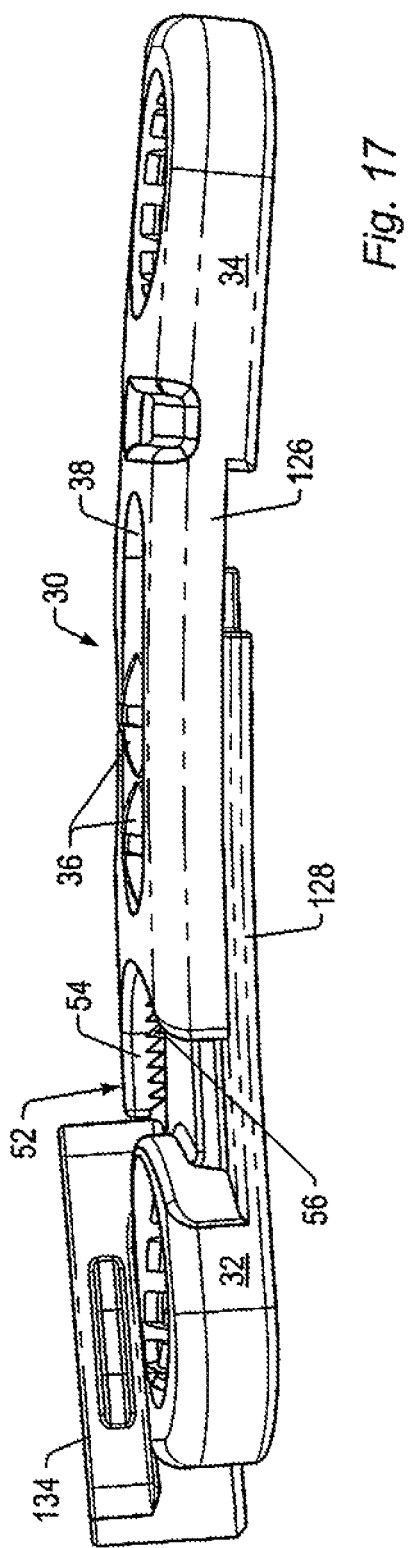
FIG. 17 depicts a side view of an embodiment of spinal compression plate with a spacer.

FIG. 17 depicts a side view of an embodiment of spinal compression plate 30. Spinal compression plate 30 may be expanded before insertion to accommodate settling and/or subsidence after installation of the spinal compression plate. Protrusion 56 positioned on underlay section 128 of first plate 32 may engage serrations 54 on overlay section 126 of second plate 34. Spinal compression plate 30 may have a curvature to accommodate lordotic curvature of a spine. Spinal compression plate 30 may have spacer 134, coupling cavity 38, one or more coupling members 36, and/or movement mechanism 52 to restrict movement between first plate 32 and second plate 34.

Spacer 134 depicted in FIG. 16 and FIG. 17 may be used to establish an initial separation distance between first plate 32 and second plate 34 of spinal compression plate 30 (i.e., establish an initial length of an adjustable-length spinal compression plate). Spacer 134 may be removed from spinal compression plate 30 before insertion of the plate into a patient. In other embodiments, a spacer used to establish an initial separation distance between plates of a spinal compression plate may remain coupled to the spinal compression plate during a portion of an insertion procedure. In some embodiments, a spacer may be used during an insertion procedure to guide placement of a spinal compression plate in a patient. In certain embodiments, a portion of a spacer may be used to position a fastener guide for placement and angulation of holes for fasteners.

Figure 18:
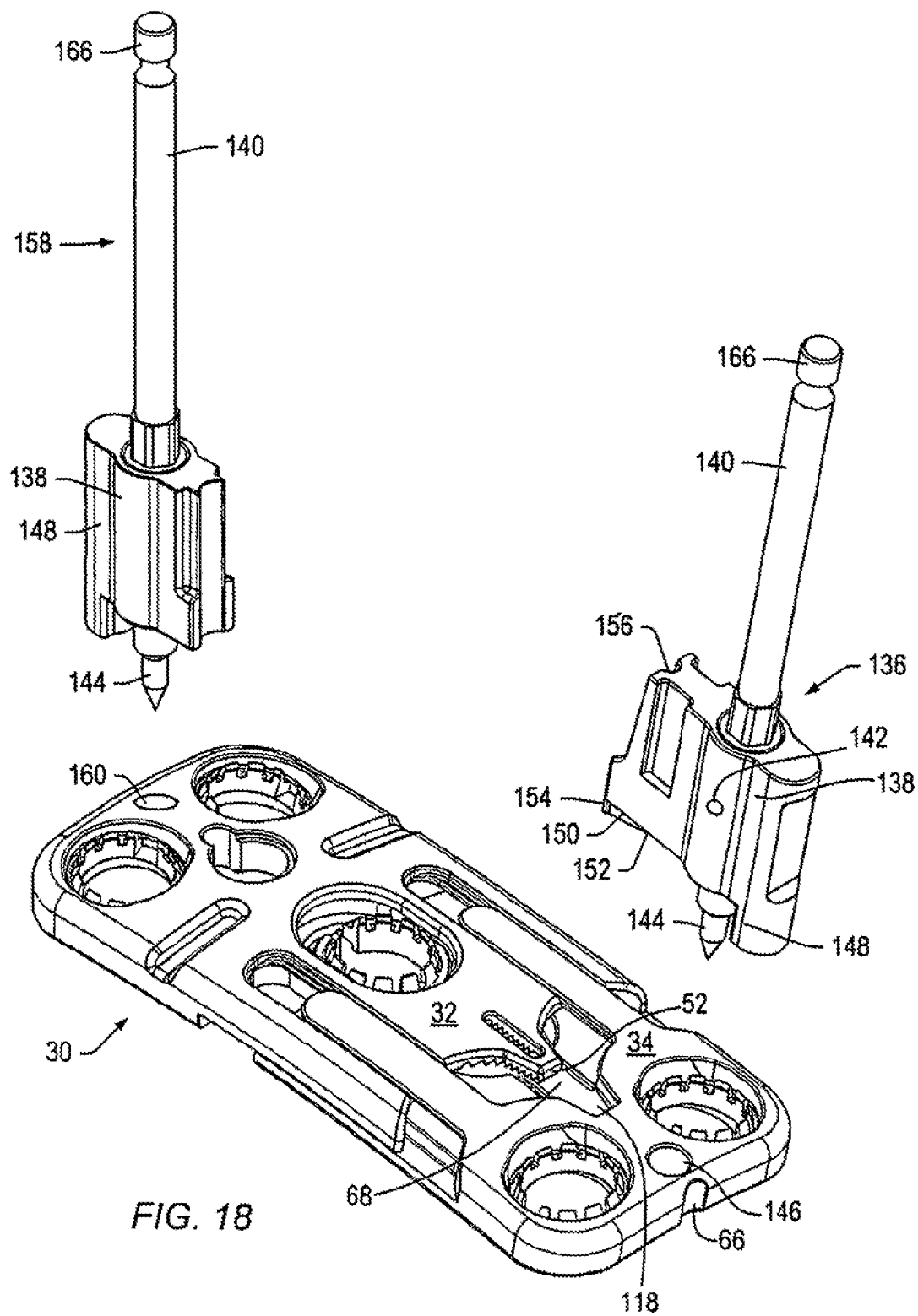
FIG. 18 depicts a perspective view of a spacer and a positioner aligned for insertion in a spinal compression plate.

FIG. 18 depicts spacer 136 aligned for coupling to spinal compression plate 30. Spacer 136 may include body 138 and guidepost 140. Pin 142 may couple guidepost 140 to spacer 136 (i.e., inhibit removal of the guidepost from the spacer) while allowing rotational and longitudinal movement of the guidepost. Rotational movement of guidepost 140 in spacer 136 may be unrestricted, while longitudinal movement of the guidepost in the spacer may be limited. Insertion end 144 of guidepost 140 may be sized for insertion into opening 146 of spinal compression plate 30. Alignment portion 148 of spacer 136 may be sized for positioning in indention 66 of spinal compression plate 30. Positioning of alignment portion 148 in indention 66 may promote coupling of spacer 136 to spinal compression plate 30. Separator 150 of spacer 136 may fit in cavity 118 to establish an initial separation distance between first plate 32 and second plate 34 of spinal compression plate 30. In some embodiments, separator 150 may overlay arm 68 of second plate 34.

In some embodiments, insertion end 144 of guidepost 140 may be pointed. Insertion end 144 of guidepost 140 may have sharpness sufficient to penetrate a vertebra of a patient to temporarily couple spinal compression plate 30 to the vertebra. In some embodiments, opening 146 of spinal compression plate 30 may have a smooth inner surface. In some embodiments, insertion end 144 of guidepost 140 may be keyed or threaded to temporarily attach to the spinal compression plate. In certain embodiments, insertion end 144 of guidepost 140 may be threaded above a pointed region. Opening 146 may have threading complementary to threading of insertion end 144 of guidepost 140. Insertion end 144 of guidepost 140 may be fastened (e.g., threaded) into opening 146 to affix spacer 136 to spinal compression plate 30.

Placement of alignment portion 148 in indention 66, and insertion of insertion end 144 in opening 146 of expanded spinal compression plate 30, may hold securing end 152 of separator 150 against second plate 34. Securing end 152 of separator 150 may fit in cavity 118 of second plate 34. Securing end 152 may have a shape complementary to a shape of cavity 118. With spacer 136 secured to second plate 34 of expanded spinal compression plate 30, first plate 32 may be moved toward the second plate such that an edge of movement mechanism 52 of the first plate contacts contacting end 154 of separator 150. Contacting end 154 of separator 150 may have groove 156. An edge of movement mechanism 52 of first plate 32 may have a shape complementary to groove 156, such that the projection fits securely in the groove. With securing end 152 of separator 150 against second plate 34 and an edge of movement mechanism 52 of first plate 32 against contacting end 154 of separator 150, a separation distance of first plate 32 and second plate 34 equal to a length of separator 150 may be achieved.

FIG. 18 depicts positioner 158 aligned above opening 160 of first plate 32 of spinal compression plate 30. Positioner 158 may have body 138 with alignment portion 148 and guidepost 140. Insertion end 144 of guidepost 140 may be pointed and/or threaded. Insertion end 144 of guidepost 140 may be inserted through opening 160 of first plate 32. Positioner 158 may be secured to spinal compression plate 30 in a manner similar to that described for spacer 136. In some embodiments, insertion end 144 of guidepost 140 may penetrate a vertebra of a patient. Positioner 158 may hold spinal compression plate 30 in place temporarily during insertion of the plate. Guidepost 140 may be used to position a fastener guide for placement and angulation of holes for fasteners.

Figure 19:
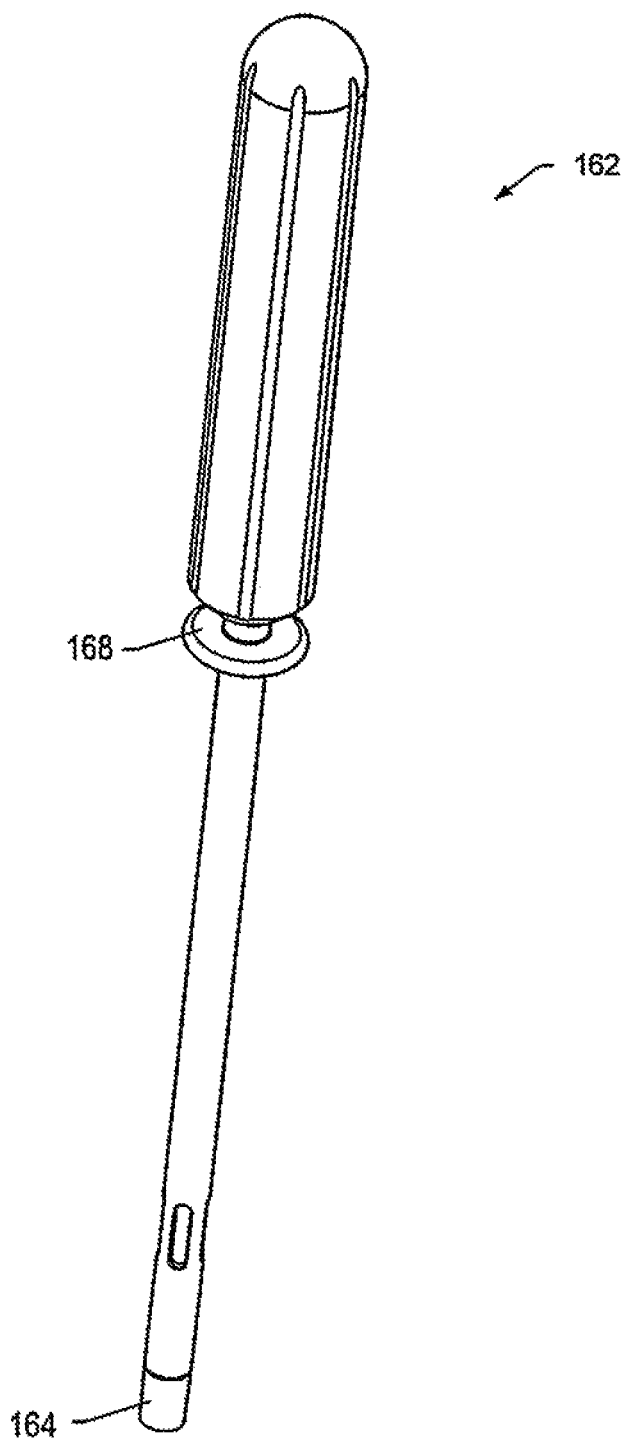
FIG. 19 depicts a perspective view of a handle for engaging a guidepost.

Handle 162, depicted in FIG. 19, may be affixed to guidepost 140. Handle 162 may be used to position a spinal compression plate that guidepost 140 is coupled to during an insertion procedures. After positioner 158 is secured to spinal compression plate 30, insertion end 164 of handle 162 may be affixed to attachment end 166 of guidepost 140. Release 168 may be activated to disconnect handle 162 from guidepost 140 after positioning spinal compression plate 30. In some embodiments, release 168 may be pulled towards a grip of handle 162 to release disconnect the handle from a guidepost positioned in insertion end 164.

Figure 20:
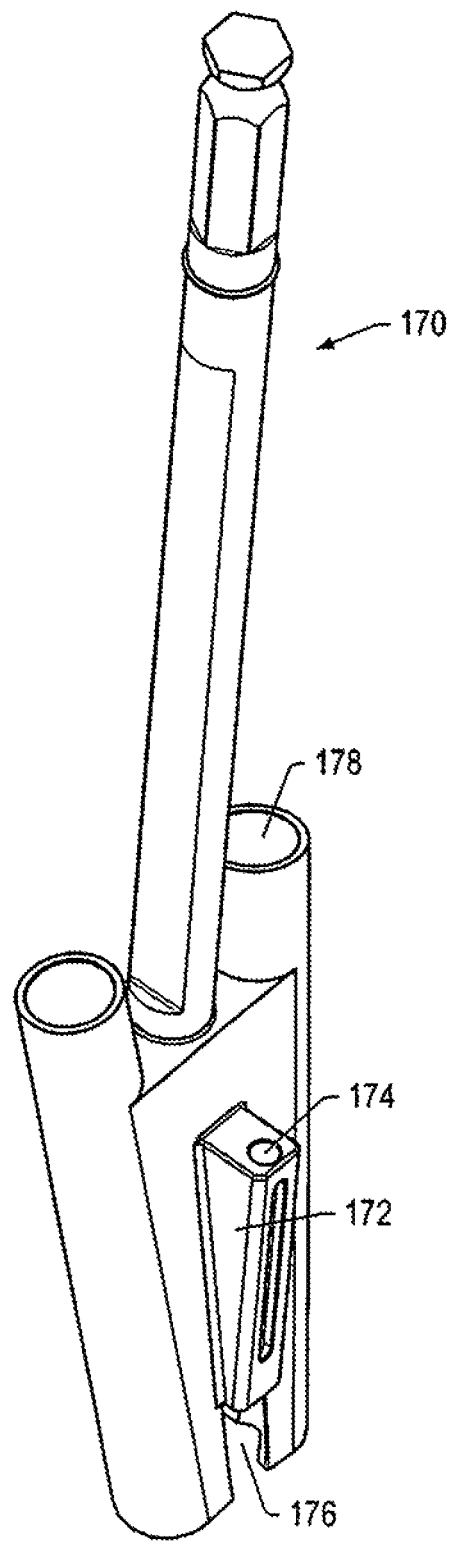
FIG. 20 depicts a perspective view of a fastener guide.

A fastener guide for positioning an instrument designed to facilitate insertion of fasteners in bone may be affixed to a guidepost. An embodiment of a fastener guide is depicted in FIG. 20. Fastener guide 170 may include guidepost holder 172 with through hole 174. A guidepost of a positioner or spacer may fasten securely in through hole 174 of guidepost holder 172. A body of a positioner or a spacer may fit securely in slot 176 of fastener guide 170. Fastener guide 170 may have hollow guide members 178. Distal openings of hollow guide members 178 may align with fastener openings in a spinal compression plate. An instrument inserted in hollow guide member 178 may pass through a fastener opening in a spinal compression plate to form a hole for a fastener. After one or more holes are formed as needed, fastener guide 170 may be removed from a guidepost of a spacer or a positioner. In some embodiments, a tap may be inserted through hollow guide member 178 to form threading in a vertebra.

Figure 21:
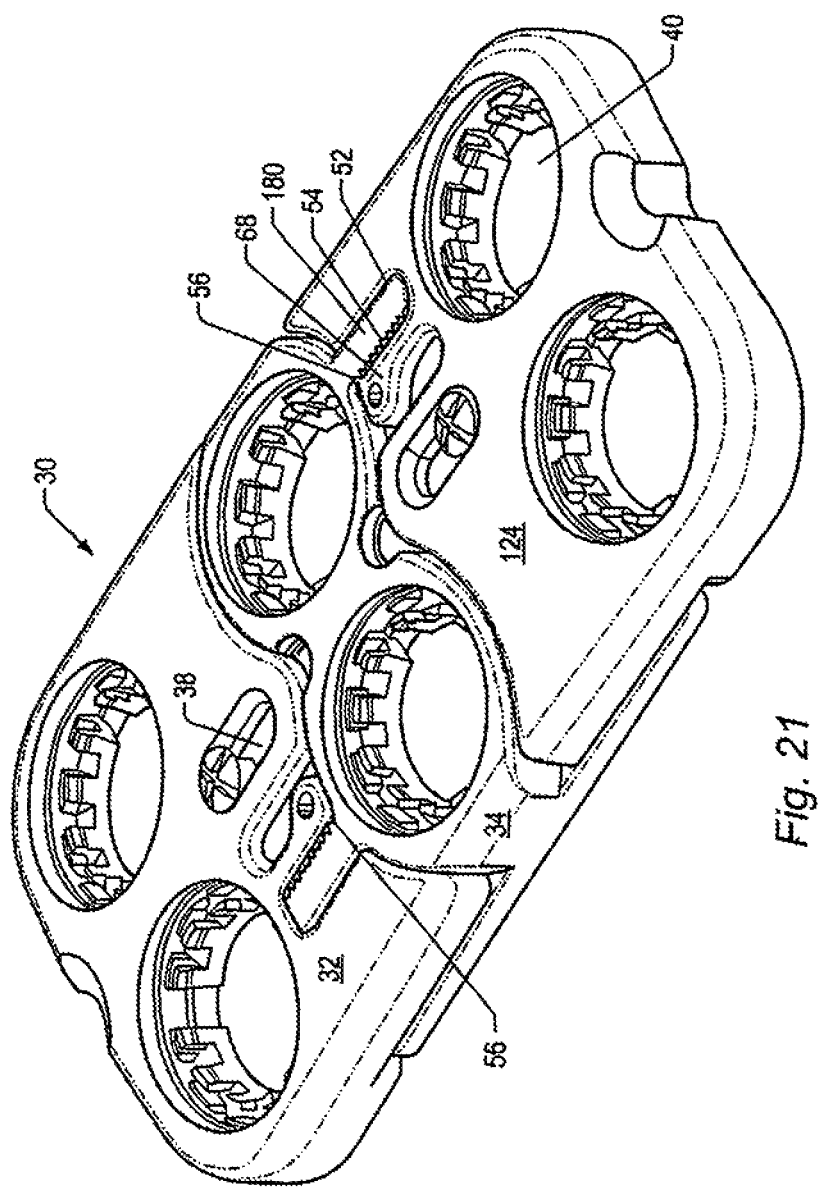
FIG. 21 depicts a perspective view of an embodiment of a spinal compression plate.

FIG. 21 depicts spinal compression plate 30 that may be used for stabilizing two vertebral levels. Spinal compression plate 30 may include first plate 32, second plate 34, and third plate 124. Plates 32, 34, 124 may include openings 40 to couple spinal compression plate 30 to vertebrae. Spinal compression plate 30 may include movement mechanism 52 with serrations 54. Movement mechanism 52 may include arm 68 with protrusion 56. Serrations 54 of extension 180 may engage protrusion 56. In some embodiments, a portion of movement mechanism 52 may be positioned on an upper surface of second plate 34. Arm 68 may have a thin section to promote deflection of the arm. As spinal compression plate 30 is compressed during use, protrusion 56 may advance and move over serrations 54. As a load on spinal compression plate 30 decreases, forces may promote expansion of the plate. In certain embodiments, a protrusion may inhibit expansion of spinal compression plate 30 during use. In some embodiments, movement mechanism 52 may be positioned on a lower side of spinal compression plate 30. As shown in the embodiment in FIG. 21, movement mechanism 52 may be positioned on lateral sides of spinal compression plate 30. In certain embodiments, movement mechanism 52 may be located in coupling cavity 38.

Figure 22:
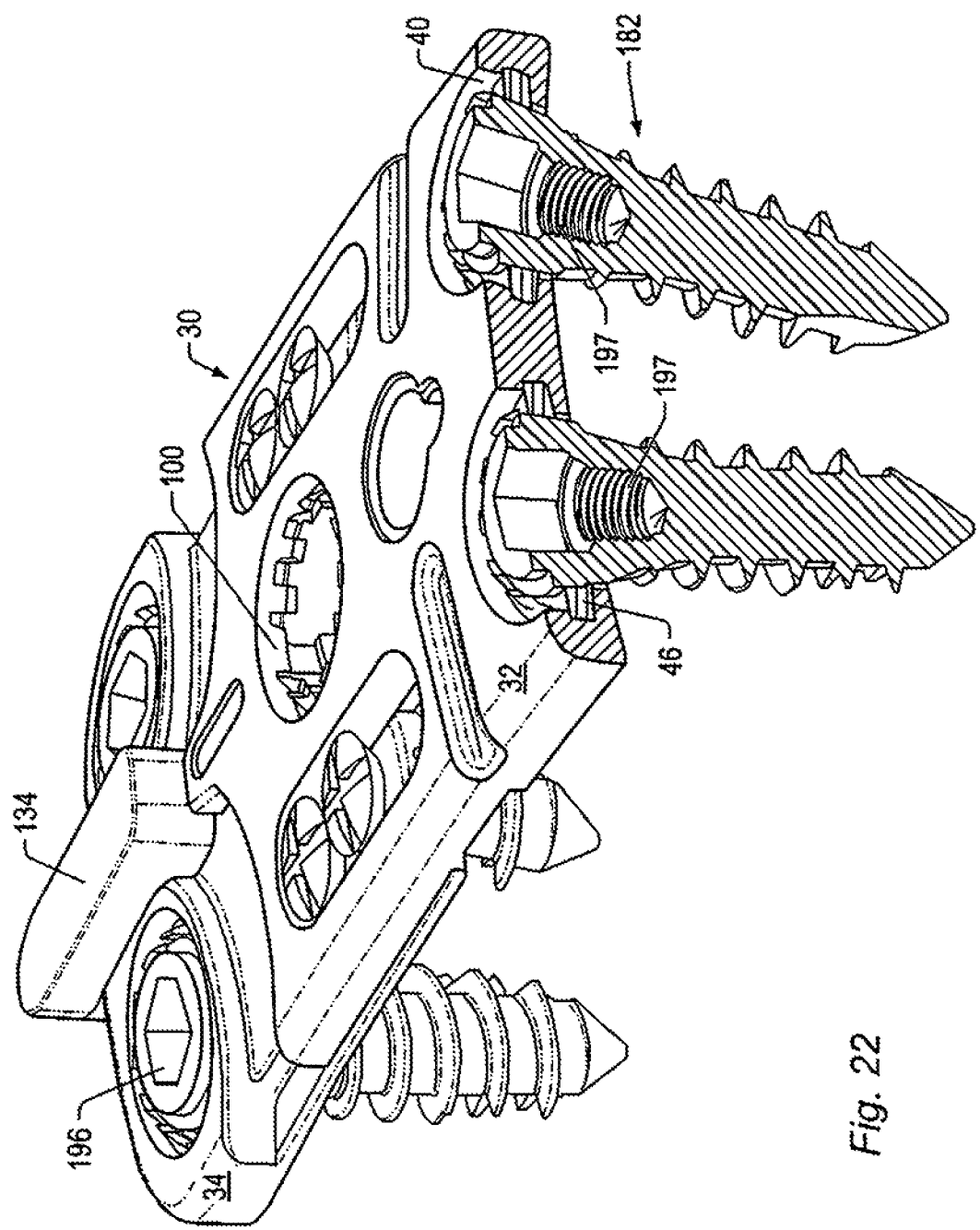
FIG. 22 depicts a perspective cross-sectional view of an embodiment of a spinal plate system.

FIG. 22 depicts a perspective cross-sectional view of an embodiment of spinal compression plate 30 including fasteners 182 and retainers 46 positioned in openings 40 of the spinal compression plate. Spinal compression plate 30 may have a curvature to match a curvature of one or more vertebrae. Spinal compression plate 30 may have spacer 134 preset to an initial separation distance between first plate 32 and second plate 34. In some embodiments, openings may be biased or angled to allow angulation of fasteners 182 into a vertebra. Fasteners 182 placed in spinal compression plate 30 may be positioned in vertebral bone in converging or diverging orientations relative to one another. In some embodiments, fasteners 182 may be placed into a vertebra so that shanks of the fasteners are oriented parallel or substantially parallel to each other.

A range of motion of a fastener may be up to 15° relative to a central axis normal to a center of opening 40 and/or center opening 100. In an embodiment, a range of motion of a fastener may be up to about 6° relative to a central axis normal to a center of opening 40 and/or center opening 100. A range of motion of a fastener may be up to about 3° relative to a central axis normal to a center of opening 40 and/or a center of center opening 100. Adjusting a difference between a height of a recess in an opening and a height of a portion of a retainer positioned in the recess may result in a larger or smaller range of motion of a fastener in the opening.

Figure 23:
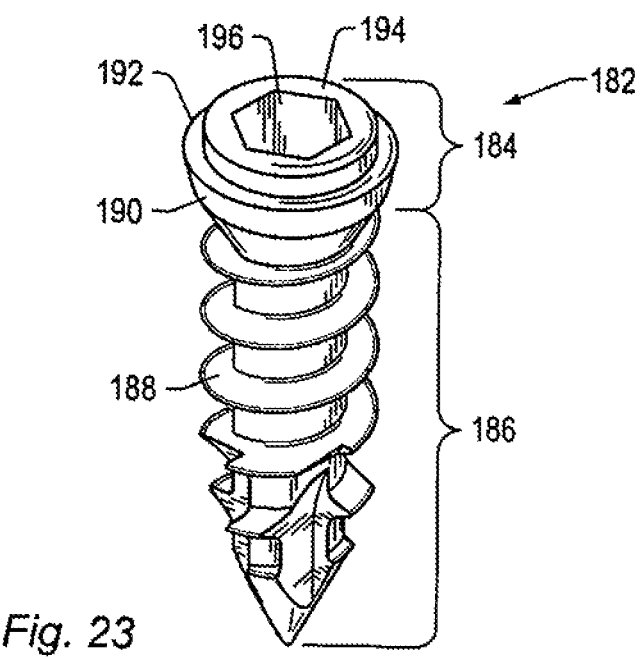
FIG. 23 depicts a perspective view of an embodiment of a fastener.

Fasteners used to couple a plate to a vertebra may include, but are not limited to, screws, nails, rivets, trocars, pins, and/or barbs. FIG. 23 depicts an embodiment of fastener 182. Fastener 182 may include head 184 and shank 186. Shank 186 may have threading 188 to engage a vertebra. Head 184 may include tapered section 190, engagement section 192, and fastening section 194. Head 184 may include tool portion 196 and recessed portion 197 (the recessed portion depicted in FIG. 22) to engage an insertion and/or removal device. Tool portion 196 may be a shape including, but not limited to, hexagonal, star-shaped, or square. In some embodiments, recessed portion 197 may have threading to engage an insertion tool and/or a removal tool. Engagement section 192 may be located at an interface of tapered section 190 and fastening section 194. Retainer projections may engage engagement section 192 to inhibit removal of fastener 182 from a spinal compression plate.

Rescue fasteners may be provided in an instrumentation set. A rescue fastener may be positioned in a deformed fastener opening in a vertebra. The rescue fastener thread may have the same thread pitch as regular fasteners. The rescue fasteners may have a larger thread major diameter and the same thread minor diameter as regular fasteners. For example, if a regular fastener has about a 4 mm major thread diameter and about a 2.5 mm minor thread diameter, a corresponding rescue fastener may have about a 4.5 mm major thread diameter and about a 2.5 mm minor thread diameter.

Rescue fasteners may be distinguished from regular fasteners in an instrumentation set. Rescue fasteners may be a distinctly different color than regular fasteners. For example, rescue fasteners may be blue while other fasteners may be silver. Different thread lengths may be indicated by different shades of a rescue fastener.

In a spinal plate system embodiment, a retainer may be positioned on a head of a fastener. An opening in a spinal compression plate for a fastener may include a recess to engage the retainer. The fastener may be inserted into the spinal compression plate with the retainer coupled to the fastener. The retainer may be compressed. As the fastener advances into bone, the retainer may expand into a recess of the opening. The fastener may be able to rotate in the opening while being driven into the bone, allowing the plate to be secured against the bone. Expansion of a retainer in a recess of an opening may inhibit backout of a fastener from a spinal compression plate if a portion of the fastener loosens from a bone.

Figure 24:
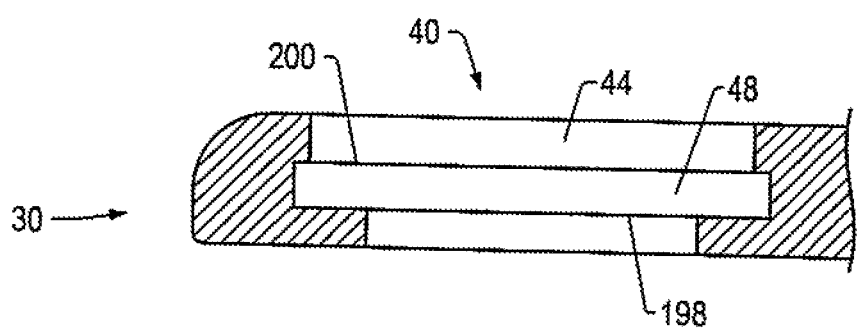
FIG. 24 depicts a cross-sectional view of an embodiment of a portion of a spinal compression plate.

FIG. 24 depicts a cross-sectional view of opening 40 of spinal compression plate 30. Opening 40 may be defined by wall 44. Wall 44 may include recess 48. A portion of a retainer (e.g., a ring) may fit in recess 48 to inhibit removal of the retainer and/or the fastener coupled to the retainer from the plate. Recess 48 may have lower shoulder 198 and upper shoulder 200. Lower shoulder 198 and upper shoulder 200 may engage a portion of a retainer to inhibit removal of the retainer from opening 40.

In some embodiments, a retainer may be able to swivel in an opening in a spinal compression plate. A reduced width of opening 40 proximate upper and lower surfaces of the opening may inhibit removal of a retainer and/or inhibit a retainer from falling out of the opening. In an embodiment, a width of opening 40 proximate upper and lower surfaces of a spinal compression plate may be less than or about equal to an outer width of a retainer to inhibit removal of the retainer from the plate. When removal of a retainer from a plate is inhibited, a risk of losing the retainers in a surgical opening during insertion may be significantly decreased and/or eliminated.

A portion of a retainer that fits in recess 48 may be thinner than a height of the recess to allow some angulation of a fastener positioned through the retainer into a vertebra. In some embodiments, a thickness of a portion of a retainer that fits in recess 48 may allow up to about 15° of angulation of a fastener positioned in the retainer. In some embodiments, a thickness of a portion of a retainer that fits in recess 48 may allow less than about 6° of angulation, less than about 2° of angulation, or substantially no angulation of a fastener positioned in the retainer.

Figure 25:
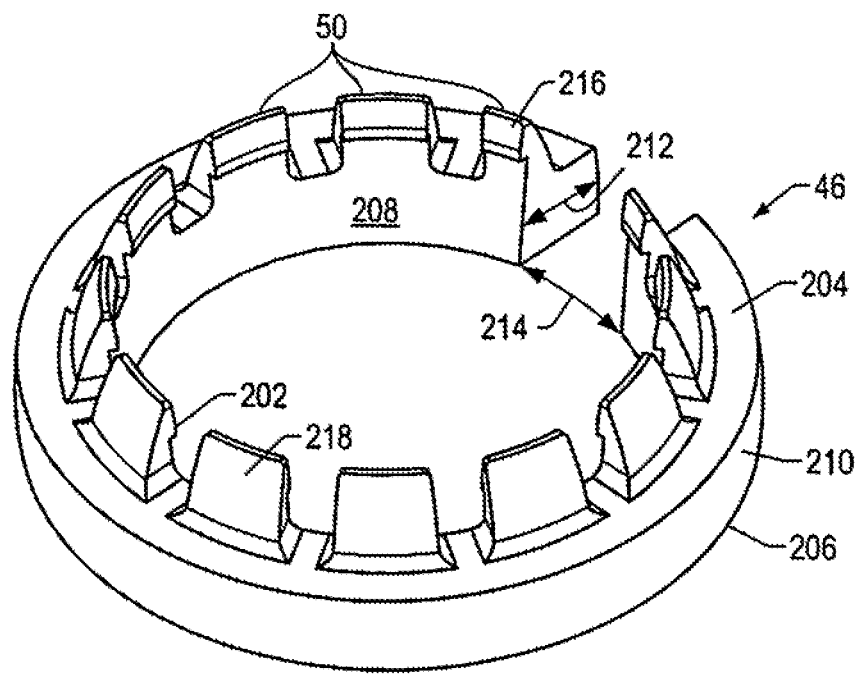
FIG. 25 depicts a perspective view of an embodiment of a retainer for a spinal compression plate.

FIG. 25 depicts an embodiment of retainer 46 in the form of a ring. Retainer 46 may have projections 50, fingers 202, upper surface 204, lower surface 206, inner surface 208, and outer surface 210. Retainer 46 may be substantially circular to surround at least a portion a fastener head. Retainer 46 may have width 212 suited to an intended application of the retainer. For example, width 212 of retainer 46 designed for insertion in an elongated opening of a spinal compression plate may exceed a width of a retainer designed for use in a substantially circular opening of a spinal compression plate. Increased width 212 of retainer 46 may enhance stability of the retainer in a recess of an opening. Enhanced stability may be advantageous for a retainer in an elongated opening.

In certain embodiments, a portion of retainer 46 may be deflectable. Retainers 46 capable of deflection may allow entry of fasteners, positioning of retainers in openings, and/or removal of retainers from openings. Retainer 46 may include gap 214 to facilitate deflection. In a spinal compression plate embodiment, a retainer positioned in an opening may radially expand as a fastener enters the opening. A retainer may contract and couple to a fastener during insertion of the fastener into the spinal compression plate.

In some embodiments, projections 50 may be spaced around retainer 46. Projections 50 may include tapered inner surface 216 to facilitate fastener entry. In addition, outer surface 218 of projections 50 of retainer 46 may be tapered to increase deflection capability of the projections. In an embodiment, fingers 202 may inhibit removal of a fastener from retainer 46 during use.

Figure 26:
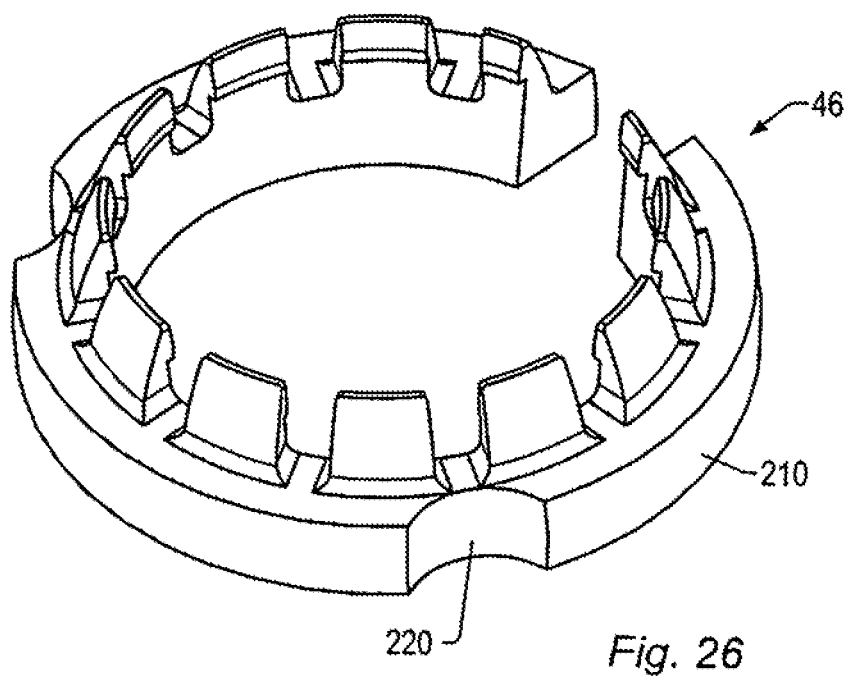
FIG. 26 depicts a perspective view of an embodiment of a retainer for a spinal compression plate.
Figure 27:
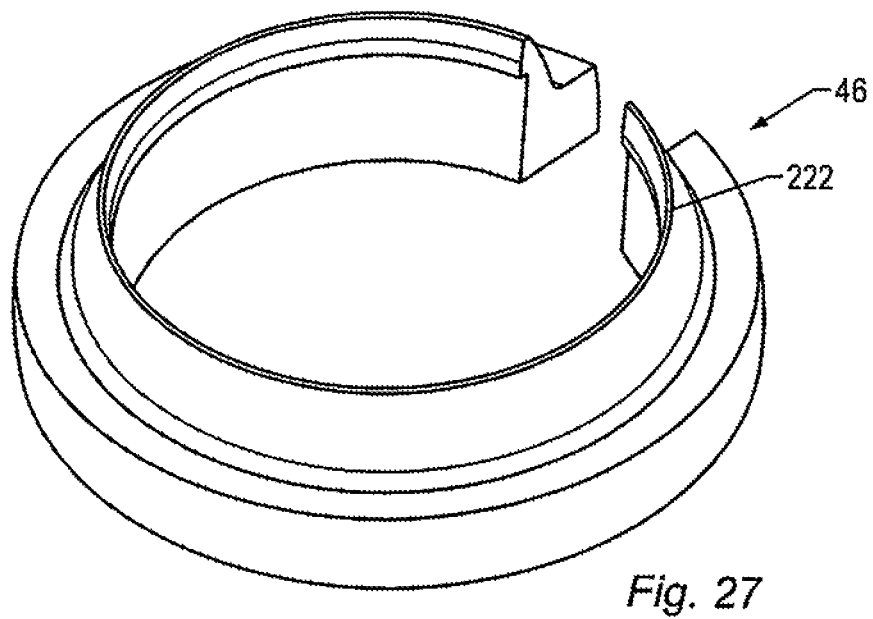
FIG. 27 depicts a perspective view of an embodiment of a retainer for a spinal compression plate.

As depicted in FIG. 26, indentions 220 may be positioned on outer surface 210 of retainer 46. Indentions 220 may increase a deflection capability of retainer 46. In some embodiments, retainer 46 may contain one or more partial slots to facilitate expansion and contraction of the retainer. Partial slots may approach, extend down to, or extend beyond a half-height of retainer 46. In some embodiments, retainer 46 may have single deflectable portion 222 depicted in FIG. 27.

Figure 28:
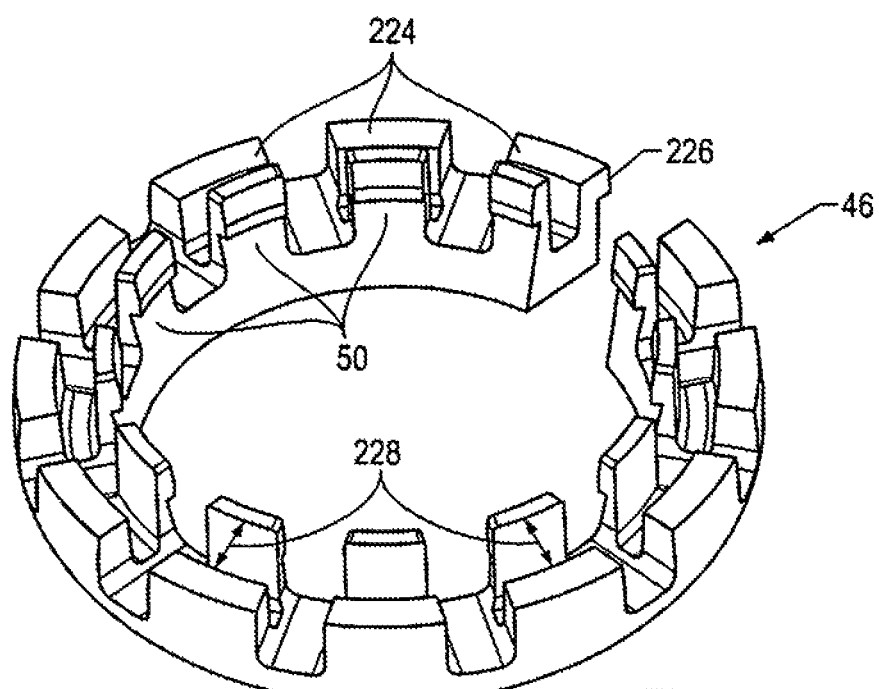
FIG. 28 depicts a perspective view of an embodiment of a retainer for a spinal compression plate.

FIG. 28 depicts retainer 46 as a ring with projections 50 and outer projections 224. In some embodiments, one or more outer projections 224 of retainer 46 may include overhang 226. Over-hang 226 of outer projections 224 may engage a recess in an opening in a spinal compression plate. Valleys 228 between projections 50 and outer projections 224 may allow deflection of the projections and the outer projections.

In some spinal compression plate embodiments, a retainer may be positioned in each opening of the spinal compression plate prior to insertion of the plate into a patient. In certain embodiments, retainers may be positioned in spinal compression plates before the plates are sent to a surgeon or hospital for insertion into a patient. In an embodiment, retainers may be provided to a surgeon independently of spinal compression plates. Before insertion of a spinal compression plate, the surgeon, or support personnel, may place retainers in openings in the spinal compression plate.

Figure 29:
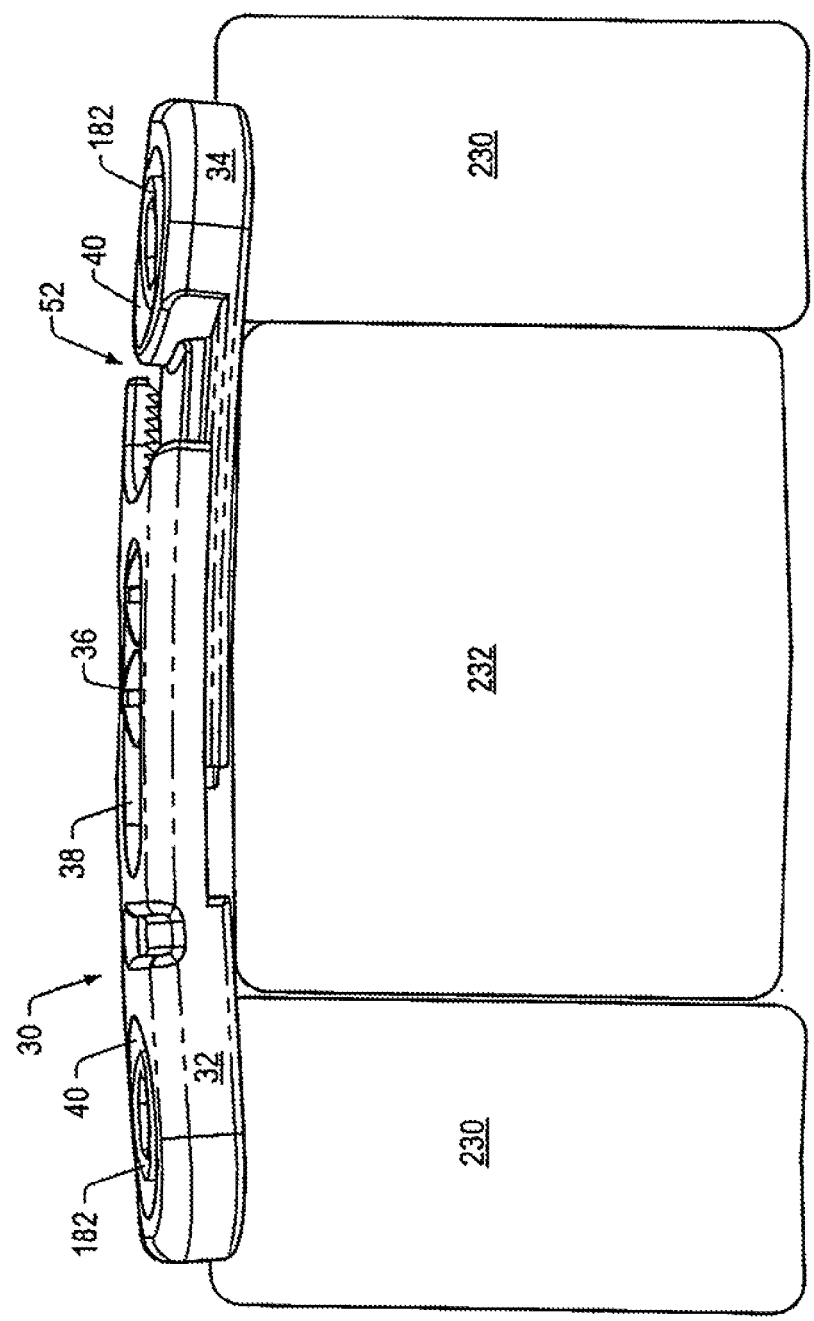
FIG. 29 depicts a side view of an embodiment of a spinal plate system coupled to two adjacent vertebrae.

FIG. 29 depicts an embodiment of spinal compression plate 30 coupled to adjacent vertebrae 230. A fastener driven through a center opening in spinal compression plate 30 may couple the spinal compression plate to spinal implant 232. In an embodiment, at least a portion of vertebral load may be transferred to a spinal implant. Maintaining at least a portion of the vertebral load on an implant may increase bone growth and increase fusion between an implant and surrounding vertebrae. Spinal implant 232 may include, but is not limited to, a bone implant (e.g., allograft), metal implants, and/or carbon fiber implants. Fasteners 182 positioned in openings 40 may couple spinal compression plate 30 to vertebrae 230.

During surgery, holes may be drilled, tapped, and/or otherwise formed in vertebrae for attachment of a spinal compression plate. The spinal compression plate may be positioned adjacent to the vertebrae. In some embodiments, a fastener may be positioned in an opening in a spinal compression plate. In an embodiment, a fastener positioned in an opening in a spinal compression plate may be advanced to drive the fastener into a vertebra. As the fastener is advanced into the vertebra, the fastener head may engage a retainer. Movement of the fastener head into the retainer may couple the fastener to the spinal compression plate.

Figure 30:
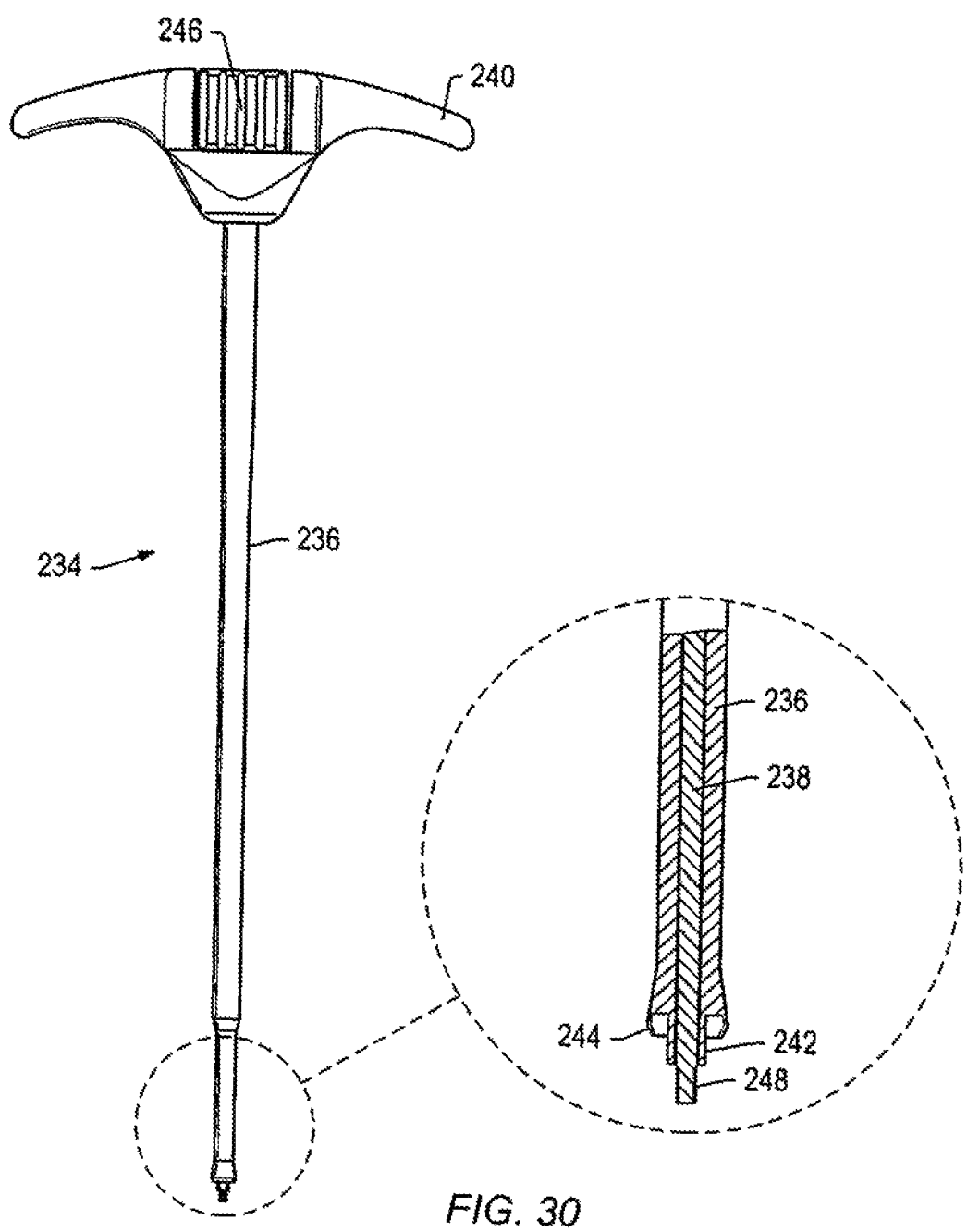
FIG. 30 depicts a front view of a fastener insertion instrument with a cross-sectional inset view that shows details of a tip of the fastener insertion instrument.

An insertion tool may be used to insert a fastener through a retainer and into a vertebra. FIG. 30 depicts an embodiment of insertion tool 234. Insertion tool 234 may include outer shaft 236 and inner shaft 238. Outer shaft 236 may include handle 240. Handle 240 may be a grip that allows a user to securely hold insertion tool 234 and easily apply sufficient torque to a fastener to drive the fastener into a vertebra. Outer shaft 236 may have sufficient length to allow handle 240 to be operated above an incision in a patient while maintaining good visibility of the operating area.

An end of outer shaft 236 may include drive section 242 and tapered section 244. Drive section 242 may mate with a tool portion of a fasteners. When drive section 242 is placed in a tool portion of a fastener, rotation of handle 240 will rotate the fastener. Tapered section 244 may contact portions of a retainer during insertion or removal of a fastener. Tapered section 244 may force fingers of a retainer outwards. Tapered section 244 may allow a fastener to be removed from the retainer.

A portion of inner shaft 238 may interact with a stop in handle 240 or another portion of outer shaft 236 to inhibit separation of the inner shaft from the outer shaft, while still allowing for some axial movement of the inner shaft relative to the outer shaft. Inner shaft 238 may have knob 246 at a first end and threaded section 248 at a second end. Threaded section 248 may mate with threading in a recessed portion of a fastener.

To use insertion tool 234, knob 246 may be moved away from drive section 242 of outer shaft 236. Drive section 242 may be placed in a recessed portion of a fastener. Knob 246 may be moved toward drive section 242 and rotated so that threaded section 248 of inner shaft 238 engages threading in a recessed portion of the fastener. Attaching threaded section 248 of inner shaft 238 to threading in a recessed portion of the fastener couples the fastener to insertion tool 234 and inhibits unintentional separation of the fastener from the insertion tool.

Insertion tool 234 may be used to position the fastener through a retainer positioned in a spinal compression plate. Handle 240 of insertion tool 234 may be rotated to drive the fastener into a vertebra. Handle 240 may be rotated until interaction of the fastener with the retainer and/or the spinal compression plate draws the spinal compression plate against the vertebra. Knob 246 may be rotated in a direction to separate threading of inner shaft 238 from threading in the recessed portion of the fastener. Insertion tool 234 may then be removed from the fastener.

To remove a fastener from a vertebra and from a spinal compression plate, drive section 242 of insertion tool 234 may be placed in the opening of the fastener to be removed. Knob 246 may be rotated to engage threading of inner shaft 238 with threading in a recessed portion of the fastener. Knob 246 may include indicia that indicate the proper rotational direction to turn the knob to couple inner shaft 238 to the fastener. As threading of inner shaft 238 engages threading in the fastener, tapered section 244 of outer shaft 236 may force fingers of the retainer outwards. When the inner shaft is secured to the fastener, handle 240 may be rotated to remove the fastener from the vertebra, spinal compression plate, and retainer.

A spinal compression plate may be used to stabilize a portion of a spine. A discectomy may be performed to remove all or a portion of a damaged intervertebral disc. The approach to the intervertebral disc may be an anterior or lateral approach. One or more spinal implants may be inserted into the disc space formed by the discectomy.

A spinal compression plate having an appropriate lordotic and radial curvature may be chosen. If needed, plate benders may be used to adjust the curvature of the spinal compression plate to conform to the curvature of vertebrae that the spinal compression plate is to be attached to. A separation distance between a first plate and a second plate may be chosen. In some embodiments, no separation is desired, and a fully compressed spinal compression plate may be inserted into a patient. In other embodiments, a spacer may be used to establish the desired separation distance. In some embodiments, a spacer and a positioner may be coupled to the spinal compression plate.

The spinal compression plate may be attached to a handle and/or a plate insertion instrument. The handle and/or plate insertion instrument may be used to position the spinal compression plate at a desired location on the vertebrae so that the spinal compression plate will inhibit expulsion of the spinal implant or spinal implants from the vertebrae. The spinal compression plate may be temporarily coupled to the vertebrae. In an embodiment, pointed ends of portions of the spacer and/or the positioner may temporarily fix the spinal compression plate to the vertebrae. In some embodiments, protruding members positioned in openings of the spinal compression plate may be used to temporarily fix the spinal compression plate to the vertebrae.

In some embodiments, a guide may be used to form openings in the vertebrae for fasteners. In some embodiments, a surgeon may form openings for the fasteners without the use of a guide.

A fastener may be attached to a fastener insertion tool. The fastener may be inserted into an opening in the spinal compression plate. The fastener insertion tool may be used to drive the fastener into an opening in a vertebra. The fastener insertion tool may be disconnected from the fastener. When the fastener insertion tool is removed from the fastener, a portion of a retainer in the opening may extend over a head of the fastener. Should the fastener loosen within the opening in the vertebra, contact between the portion of the retainer and the fastener head will inhibit backout of the fastener from the opening in the spinal compression plate. The fastener insertion tool may be used to insert additional fasteners into openings in the spinal compression plate to secure the plate to the vertebrae.

The spacer and the positioner may be removed from the spinal compression plate. The surgery opening may be closed. At a later time, should portions of the vertebrae that the spinal compression plate is attached to subside and/or settle, a first plate of the spinal compression plate may move towards a second plate. Movement of the first plate towards the second plate may accommodate subsidence and/or settling of the vertebrae.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed:

1. A spinal plate assembly for stabilizing a spinal segment of a spine, the spinal plate assembly comprising:
    a spinal compression plate including:
        a first plate including one or more openings for receiving vertebral fasteners to secure the first plate to a first vertebra;

a second plate coupled to the first plate, the second plate including one or more openings for receiving vertebral fasteners to secure the second plate to a second vertebra;
a locking mechanism including a first surface on the first plate and a second surface on the second plate, wherein the first and second surfaces are configured to engage each other to allow the first and second plates to move toward each other and to prohibit the first and second plates from moving away from each other; and
a removable spacer positioned between a portion of the first plate and a portion of the second plate, the removable spacer configured to position the first plate at a first position relative to the second plate to retain the spinal compression plate at a first length;
wherein upon removing the removable spacer the first plate is permitted to slide toward the second plate to reduce the length of the spinal compression plate.

2. The spinal plate assembly of claim 1, wherein the removable spacer is configured to establish an initial separation distance between the portion of first plate and the portion of the second plate.

3. The spinal plate assembly of claim 2, wherein the spacer allows for an initial separation distance of about 8 millimeters between the portion of the first plate and the portion of the second plate.

4. The spinal plate assembly of claim 2, wherein the spacer allows for an initial separation distance of about 4 millimeters between the portion of the first plate and the portion of the second plate.

5. The spinal plate assembly of claim 1, wherein the locking mechanism is a ratcheting mechanism.

6. The spinal plate assembly of claim 1, wherein upon removal of the spacer, the first plate is permitted to slide relative to the second plate to a second position, the spinal compression plate having a length at the second position less than the length at the first position.

7. The spinal plate assembly of claim 6, wherein at the second position, the portion of the first plate is permitted to abut the portion of the second plate.

8. The spinal plate assembly of claim 1, wherein the first surface is configured to face the vertebra and the second surface is configured to face away from the vertebra when the assembly is secure to first and second vertebrae.

9. A spinal plate assembly for stabilizing a spinal segment of a spine, the spinal plate assembly comprising:
a spinal compression plate including:
a first plate including one or more openings for receiving vertebral fasteners to secure the first plate to a first vertebra;
a second plate coupled to the first plate, the second plate including one or more openings for receiving vertebral fasteners to secure the second plate to a second vertebra;
a uni-directional movement mechanism that permits movement of the first plate toward the second plate from a first position to a second position, but prohibits movement of the first plate away from the second plate; and
a removable spacer removably coupled between the first plate and the second plate, the removable spacer configured to position the first plate at the first position during installation of the spinal compression plate onto the spinal segment of the spine;
wherein upon removing the removable spacer the first plate is permitted to slide relative to the second plate toward the second position, but the first plate is prohibited from moving away from the second plate.

10. The spinal plate assembly of claim 9, wherein the spacer allows for an initial separation distance of about 8 millimeters between the first plate and the second plate.

11. The spinal plate assembly of claim 9, wherein the spacer allows for an initial separation distance of about 4 millimeters between the first plate and the second plate.

12. The spinal plate assembly of claim 9, wherein the uni-directional movement mechanism is a ratcheting mechanism.

13. The spinal plate assembly of claim 9, wherein the spinal compression plate has a first length at the first position and a second length at the second position, the second length being less than the first length.

* * * * *